US009488599B2

(12) United States Patent
Augustine et al.

(10) Patent No.: US 9,488,599 B2
(45) Date of Patent: Nov. 8, 2016

(54) AUTHENTICATION DEVICE FOR FULL INTACT WINE BOTTLES

(75) Inventors: Matthew P. Augustine, Davis, CA (US); Stephen J. Harley, Davis, CA (US); Victor Lim, Davis, CA (US); Paul Stucky, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1009 days.

(21) Appl. No.: 12/927,411

(22) Filed: Nov. 12, 2010

(65) Prior Publication Data

US 2011/0184681 A1  Jul. 28, 2011

Related U.S. Application Data

(60) Provisional application No. 61/281,185, filed on Nov. 13, 2009.

(51) Int. Cl.
| G06F 17/18 | (2006.01) |
| G01R 27/28 | (2006.01) |
| G01R 23/00 | (2006.01) |
| G01N 22/00 | (2006.01) |
| G01N 33/14 | (2006.01) |
| G01R 33/12 | (2006.01) |
| G01N 33/00 | (2006.01) |
| G01N 27/22 | (2006.01) |

(52) U.S. Cl.
CPC .......... *G01N 22/00* (2013.01); *G01N 27/221* (2013.01); *G01N 33/00* (2013.01); *G01N 33/14* (2013.01); *G01N 33/146* (2013.01); *G01R 33/12* (2013.01)

(58) Field of Classification Search
CPC .. G01N 22/00; G01N 33/146; G01N 27/221; G01N 30/8665; G01N 9/002; G01N 9/36; G01N 24/08; G01F 1/74; G01R 23/02; G01R 33/44; G01R 33/34053; G01R 33/022; G01M 3/329; G01V 3/14
See application file for complete search history.

(56) References Cited

U.S. PATENT DOCUMENTS

| 5,603,322 | A | * | 2/1997 | Jesmanowicz ..... | G01R 33/4806 324/309 |
| 6,606,566 | B1 | | 8/2003 | Sunshine | |
| 7,138,801 | B2 | | 11/2006 | Yamamoto et al. | |
| 7,339,377 | B2 | | 3/2008 | Augustine et al. | |
| 7,394,262 | B2 | | 7/2008 | Manneschi | |
| 2005/0073310 | A1 | | 4/2005 | Weatherall et al. | |
| 2007/0001673 | A1 | * | 1/2007 | Augustine .............. | G01N 24/08 324/307 |
| 2008/0297156 | A1 | | 12/2008 | Suematsu et al. | |

OTHER PUBLICATIONS

Garwood et al., Advances in Magnetic Resonance—The Return of the Frequency Sweep: Designing Adiabatic Pulses for Contemporary NMR, Journal of Magnetic Resonance 153, pp. 155-177.*
PCT Search Report from Application No. PCT/US2010/002962, dated Jan. 11, 2011.

* cited by examiner

*Primary Examiner* — Sujoy Kundu
*Assistant Examiner* — L. Anderson
(74) *Attorney, Agent, or Firm* — Kilpatrick Townsend & Stockton LLP

(57) ABSTRACT

Methods, devices and systems for identifying or authenticating an intact bottle of wine are provided.

16 Claims, 7 Drawing Sheets

AUTHENTICATION DEVICE FOR FULL INTACT WINE BOTTLES

CROSS REFERENCE TO RELATED APPLICATIONS

This application claims priority to and benefit of: Augustine et al., AN AUTHENTICATION DEVICE FOR FULL INTACT WINE BOTTLES, U.S. Ser. No. 61/281,185, filed Nov. 13, 2009. The full disclosure of this prior application is incorporated by reference herein in its entirety.

FIELD OF THE INVENTION

The invention is in the field of sealed container analysis, e.g., of intact wine bottles. Methods and systems that can be used to analyze sealed containers such as an intact bottle of wine, e.g., a full unopened bottle of wine, are provided. For example, a low frequency spectrometer capable of non-invasively and non-destructively screening the dielectric or diamagnetic properties of full intact bottles of wine is described. When used with principal component analysis, the spectrometer can be used to identify counterfeit wine or contaminants, such as illegal or hazardous substances, in sealed containers.

BACKGROUND OF THE INVENTION

Counterfeiting has become commonplace in contemporary society and the wine industry, a multibillion dollar market, is no exception. (Group, M. A. a. A., World Wine Situation and Outlook. In Agriculture, U.S. D. o., Ed. 2006; Vol. 2009.) The combination of rare wine value, often demanding in excess of $5,000 per bottle, with the sharp rise in wine counterfeiting has attracted the attention of the Federal Bureau of Investigation. (Wilke, J. R., U.S. Investigates Counterfeiting of Rare Wines. *The Wall Street Journal* Mar. 6, 2007.) The list of counterfeit suspects is not just limited to individual private wine collectors, as auction houses have also been implicated for the distribution of faux wine (Frank, M., Counterfeit Bottles Multiply as Global Demand for Collectable Wine Surges. *Wine Spectator* Jan. 31-Feb. 28, 2007). This suggests that the problem corrupts both the supply and demand sides of the high end wine market. Attempts have been made to address this issue by using special labels (Locke, M. High-tech Systems Cork Counterfeit Wine. USA today.com website on the world wide web in news/techinnovations/2007-06-06-counterfeit-wine); however, the practiced counterfeiter easily defeats these measures by carefully draining these specially marked bottles and refilling with lower quality wine.

It is clear that the high end wine market is in desperate need of a technology that is capable of verifying the contents of a sealed bottle of wine, e.g., a rare, collectible wine bottle. Traditional spectroscopic absorption methods used to study molecular structure including ultra-violet/visible, infrared, and microwave as well as electron and nuclear spin resonance methods, mass spectrometry, and x-ray absorption are capable of fingerprinting wine. However, with the exception of four studies all of these approaches violate the wine bottle cork and seal, thus devaluing the wine. These approaches are obviously not attractive to investors spending several thousands of dollars for a single bottle. Both the intact bottle infrared (Cozzolino, D. Non-Destructive Analysis by VIS-NIR Spectroscopy of Fluid(s) in its original container. 2005), Raman (Eliasson, C.; Macleod, N. A.; Matousek, P., Non-invasive Detection of Cocaine Dissolved in Beverages Using Displaced Raman Spectroscopy. *Analytica Chimica Acta* 2008, 607, 50-53), and mass spectrometry (Lim, V.; Harley, S.; Augustine, M. P., A Screening Device for Full Intact Cork Tainted Wine Bottles. Manuscript in Progress.) based methods are not likely candidates for wine fingerprinting due to a variety of problems. For example, the infrared method suffers from bottle-to-bottle variations in glass composition and surface morphology leading to difficulties in coupling light into and out of the wine bottle. The developed methods eliminate this issue with ring electrodes. The Raman method requires large sample concentrations to overcome signal-to-noise issues. The mass spectrometry method is limited to probing cork born compounds like 2,4,6-trichloroanisole. The most promising of these four methods involves combining the full wine bottle nuclear magnetic resonance (NMR) approach developed to study oxidative wine spoilage (Weekley, A. J.; Briuns, P.; Augustine, M. P., A Nondestructive Method of Determining Acetic Acid Spoilage in an Unopened Bottle of Wine. *Journal of Enology and Viticulture* 2003, 53, 18-3214; Weekley, A. J.; Briuns, P.; Sisto, M.; Augustine, M. P., Using NMR to Study Full Intact Wine Bottles. *Journal of Magnetic Resonance* 2003, 161, 91-98.) with small sample NMR methods used to fingerprint wine. The small sample studies use NMR spectroscopy to monitor amino acid ratios (Carpentieri, A.; Gennaro, M.; Amoresano, A., Rapid Fingerprinting of Red Wines by MALDI Mass Spectrometry. *Analytical and Bioanalytical Chemistry* 2007, 389, 969-982.) or the partitioning of deuterium among the methyl and ethyl groups in ethyl alcohol and water (Martin, G. J.; Guillou, C.; Martin, M. L.; Cabanis, M. T.; Tep, Y.; Aerny, J., Natural Factors of Isotope Fractionation and the Characterization of Wines. *Journal of Agricultural and Food Chemistry* 1988, 36, 316-322.) along with rare element abundance (Lutz, O., Ascertainment of Boric Acid Esters in Wine by 11B NMR. *Naturwissenschaften* 1991, 78, 67-69; Greenough, J. D.; Jackson, H. P.; Longerich, H. P., Element Fingerprinting of Okanagain Valley Wines Using ICP-MS: Relationship Between Wine Composition, Vineyard, and Wine Color. *Australian Journal of Grape and Wine Research* 1997, 75-83.) in wine to provide region specific fingerprinting. Although the preliminary testing of a full wine bottle NMR based authentication approach that exploits the relative concentration of ethyl alcohol, acetic acid, succinic acid, proline, and three borate esters in wine is promising, the method is complicated and requires the use of bulky equipment that cannot be made portable with existing technology. (Sobieski, D. N. From Ion Channels to Wine: Using Magnetic Resonance to Probe Dynamics and Chemical Composition. University of California Davis, Davis, 2008.)

Therefore, an easy to use, e.g., portable, apparatus and method for non-destructively and non-invasively finger-printing the contents of a sealed container, such as a bottle of wine, are needed in the art.

SUMMARY OF THE INVENTION

The invention provides methods and systems for identification of the contents of a sealed, e.g., unopened intact, container, e.g., liquid contents such as wine. Such devices and methods can be used to identify and/or authenticate full intact bottles of wine or to identify illegal or hazardous contaminants in a sealed container.

The present invention provides methods, devices and systems for analyzing the contents of sealed containers, e.g., bottles of wine, and authenticating them against the contents of known containers.

In one embodiment, methods of analyzing the contents of a sealed container are provided. The methods typically comprise applying a frequency swept electric field to a probe surrounding the container; detecting a change in the electric field as a function of frequency, thereby producing one or more data set; and performing a statistical analysis on the one or more data set, thereby producing a profile of the contents of the sealed container. The statistical analysis preferably comprises principal component analysis (PCA) and the sealed container is typically a beverage container, such as a bottle of wine.

The electric field is typically a low frequency field, e.g., ranging from about 200 Hz to about 30 MHz, from about 200 Hz to about 24 MHz, or from about 500 Hz to about 30 MHz. The change in the field can comprise phase retardation or amplitude attenuation, e.g., as a function of frequency.

The probes of the invention can comprise electrodes, e.g., circular copper electrodes or coils, e.g., solenoid coils. For example, the probe can be a pair of electrodes such as a first annular electrode surrounding the container at a first position and a second annular electrode surrounding the container at a second position. Another example probe comprises an outer coil and first and second inner coils, into which the container is positioned. The first and second inner coils are positioned within the outer coil and the container is positioned within the inner two coils.

In one aspect, the methods can be used to authenticate a test bottle of wine. An example method comprises measuring a change in an electric or magnetic field when applied to a standard bottle of wine positioned within an annular probe, thereby producing a first set of data; measuring a change in an electric or magnetic field when applied to a test bottle of wine positioned within the probe, thereby producing a second set of data; applying statistical analysis to the first and second set of data to produce a first profile and a second profile and comparing the first profile and the second profile, thereby determining if the test bottle of wine is the same as the standard bottle of wine.

In one aspect, the probe is a pair of circular electrodes and the frequency of the electric field ranges from about 200 Hz to about 24 MHz. In another aspect, a magnetic field is applied using a frequency swept electric field applied to a solenoid surrounding the bottle, wherein the frequency of the electric field ranges from about 500 Hz to about 30 MHz.

In another embodiment, the invention provides an apparatus for analyzing the contents of a sealed container, e.g., a full intact bottle of wine. The apparatus typically comprises a waveform generator, which waveform generator is capable of producing a frequency swept electrical field; a first annular electrode operably coupled to the waveform generator, which first annular electrode contacts the container at a first position; a second annular electrode which contacts the container at a second position; and, a receiver operably coupled to the second electrode, which receiver is capable of detecting the electric field at the second electrode.

In another embodiment, an apparatus for analyzing a sealed container, e.g., a beverage bottle comprises a waveform generator, which waveform generator is capable of producing a frequency swept electrical field; a first solenoid coil operably coupled to the waveform generator, which solenoid produces a magnetic field; a second sample solenoid coil and a third reference solenoid coil positioned within the first coil, wherein the container can be positioned within the second coil, and a receiver operably coupled to the second sample coil, which receiver is capable of detecting a change in the magnetic field due to the contents of the container.

In some aspects, an apparatus of the invention further comprises a computer operably coupled to the receiver for data analysis, such as statistical analysis, e.g., PCA. An apparatus of the invention can also comprise the sealed container, e.g., a wine bottle, e.g., positioned within the second sample solenoid coil or within a pair of electrodes.

BRIEF DESCRIPTION OF THE FIGURES

FIG. 5 provides diagrams of a sample probe of the invention.

FIG. 6 is a schematic diagram of a sample apparatus of the invention.

DETAILED DESCRIPTION

Figure 1:
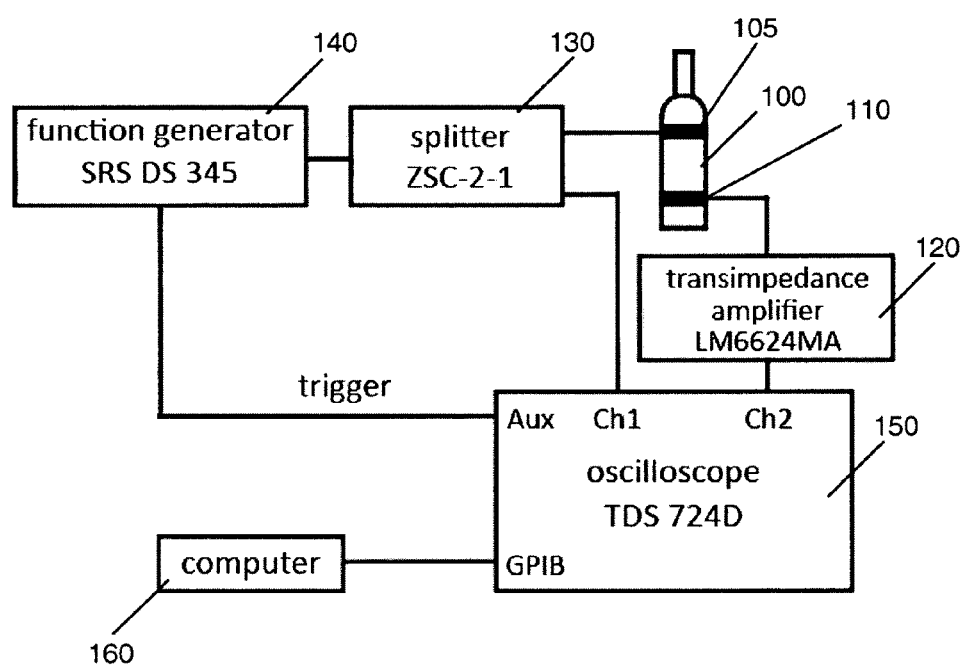
FIG. 1 is a schematic diagram of a system of the invention, e.g., one for monitoring dielectric absorption of a full intact bottle of wine or other unopened or otherwise sealed container.

The invention provides methods, devices and systems for analyzing the contents of a sealed or unopened container. A low frequency spectrometer, e.g., less than 30 MHz, can be used to non-invasively and non-destructively screen the contents of a sealed container, e.g., a beverage bottle. Methods and devices for such screening are provided herein in two preferred embodiments, along with examples of screening wine bottles. In one embodiment, the dielectric properties of the contents of a container are screened using a pair of annular electrodes to avoid container dependent characteristics. In a second embodiment, the magnetic susceptibility of the contents is screened using a solenoid and gradiometer coil system that negates any effects the container has on the result. Both embodiments use a statistical analysis of the resulting data to provide a fingerprint of the container contents. Principal component analysis is the preferred statistical method, but other methods are optionally used instead of or in addition to PCA. The sensitivity of the method to various ionic and molecular components of wine is established by the examples described below. When used with principal component analysis, the spectrometer and methods provided herein can be used, e.g., to identify counterfeit wine or to identify hazardous and/or illegal substances in sealed containers.

In one embodiment, an easily portable wine authentication method is provided based on the dielectric and/or magnetic properties of wine at low frequencies, e.g., less than 30 MHz. The frequency dependent dielectric absorption or magnetic susceptibility of wine constituents, e.g., ethyl alcohol, acetic acid, glycerol and/or potassium sulfate, leads to amplitude attenuation and/or phase retardation of an electric or magnetic field applied to the contents of a sealed container. As a frequency swept field is applied to the container, the ionic and molecular components of the substance within the container produce an effect on the field as a function of frequency. This response to the frequency swept field is detected and analyzed, e.g., using PCA to provide a fingerprint of the contents of the container, e.g., a bottle of wine. For example, the response from a rare bottle of wine suspected of being a counterfeit or being spoiled, can be compared to a known bottle of the same wine to determine if the contents are uncontaminated and/or the same as the known bottle.

A contaminant in the bottle of wine or bottle containing a different, e.g., counterfeit, wine can be detected due to differences in the identity and or concentration of various components in the wine. The cause of these differences in wine result from the motion of charged atomic and molecular ions, the electric orientation of neutral polar molecules, and the electric polarization of neutral non-polar molecules. (Kremer, F.; Schonhals, A., *Broadband Dielectric Spectroscopy*. Springer: Berlin, 2003.) The contribution of each of these mechanisms to the overall observed dielectric response is a function of the concentration of the separate components in wine, amounts that vary dramatically during the complex chemistry that occurs during grape growth and wine vinification. For example, the natural origin of metal ions accumulated during grape growth reflect both the soil composition and climate, conditions that vary from vineyard-to-vineyard and year-to-year. (Pohl, P., What do Metals Tell us about Wine? *Trends in Analytical Chemistry* 2007, 26, (9), 941-949.) Metal ions are also accumulated in grapes as they mature due to external influences as well. Pollution can introduce lead and cadmium (Galani-Nikolakai, S.; Kallithrakas-Kontos, N.; Katsanos, A. A., Trace Element Analysis of Cretan Wines and Wine Products. *Sci. Total Environ.* 2002, 285, 155); sea spray can increase sodium content (Amerine, M. A.; Thoukis, G.; Marfa, R. V., Further Data on the Sodium Content of Wines. *American Journal of Enology and Viticulture* 1953, 4, (1), 157-166); fertilizer can introduce potassium, calcium, and copper (Diaz, C.; Conde, J. E.; Estevez, S. J.; Olivero, P.; Perez Trujillo, P., Application of Multivariate Analysis and Artificial Neural Networks for the Differentiation of Red Wines from the Canary Islands According to the Island Origin. *Journal of Agricultural and Food Chemistry* 2003, 51, 4303-4308); while pesticides can elevate cadmium, copper, manganese, lead, and zinc (Nasir, F.; Jiries, A. G.; Batarseh, M. I.; Beese, F., Pesticides and Trace Metals Residue in Grape and Home Made Wine in Jordan. *Environmental Monitoring and Assessment* 2001, 66, 25-263.) concentration in mature grapes. Both inorganic atomic and small molecular ions as well as organic molecules are introduced during wine preparation. Storage vessels, pipes, and transfer vessels can alter aluminum, cadmium, chromium, copper, iron, and zinc atomic ion concentration (Kment, P.; Mihaljevic, M.; Ettler, V.; Sebek, O.; Strand, L.; Rohlova, L., Differentiation of Czech Wines using Multielement Composition—A Comparison with Vineyard Soil. *Food Chemistry* 2005, 91, 157-166.) in wine while the use of flocculants can modify the amounts of aluminum, calcium, and sodium in wine (Zoecklein, B. W.; Fugelsang, K. C.; Gump, B. H.; Nury, F. S., *Wine Analysis and Production*. Springer: 1995.) Molecular ions like calcium carbonate and sulfites are produced in wine by external pH buffering to control wine acidity (Alvarez, M.; Moreno, I. M.; Jos, M. A.; Camean, A. M.; Gonzalez, A. G., Study of Mineral Profile of Montilla-Moriles "fino" Wines using Inductively Coupled Plasma Atomic Emission Spectrometry Methods. *Journal of Food Composition Analysis* 2007, 20, 391-395) and through attempts to control spoilage and to improve long term wine stability (Eschenbruch, Sulfite and Sulfide Formation During Winemaking—A Review. *American Journal of Enology and Viticulture* 1974, 25, (3), 157-162.) It is the familiar alcoholic fermentation process that introduces ethyl alcohol, acetic acid, and sugars to wine while the malolactic fermentation conversion of malic acid to lactic acid controls the ultimate concentration of these species in wine (Wibowo, D.; Eschenbruch, R.; Davis, C. R.; Fleet, G. H.; Lee, T. H., Occurrence and Growth of Lactic Acid Bacteria in Wine: A Review. *American Journal of Enology and Viticulture* 1985, 36, 302-313). In some cases glycerol is also added to change the wine viscosity and to impart a perceived wine sweetness. (Noble, A. C.; Bursick, G. F., The Contribution of Glycerol to Perceived Viscosity and Sweetness in White Wine. *American Journal of Enology and Viticulture* 1984, 35, (2).) The removal of potassium bitartarate from American versus European wines can also change the observed wine ionic strength. (Fessler, J. H. Process of Cold Stabilization of Wine. 1978.)

After grape maturation and subsequent vinification, potassium tends to be the most prevalent atomic ion in wine (0.1-3 g/L) followed by sodium, calcium, and magnesium. (Pohl, P., What do Metals Tell us about Wine? *Trends in Analytical Chemistry* 2007, 26, (9), 941-949) The comparatively less abundant iron, copper, and manganese ions in wine catalyze oxidative processes that lead to the production of aldehydes, ketones, or carboxylic acids. (Mozaz, S. R.; Sotro, A. G.; Segovia, J. G.; Azpilicueta, C. A., Influence of Decantation of Viura Must on the Cation Content. Evolution During Wine Fermentation and Stabilization. *Food Research International* 1999, 32, 683-689.) Thus, while the direct effect of these transition metal ions on the measured dielectric response may be too small to measure, the presence of these catalytically formed carbonyl compounds modifies the measured signal. It is awareness of the different types and concentrations of ions in wine and their relative contribution to the overall wine conductivity and, thus, the dielectric or diamagnetic response that can be used to form a wine fingerprint. Other materials that contain similar components can also be analyzed with the technology provided herein. For example, brandy, cognac, other alcoholic beverages and non-alcoholic liquids, such as vinegar, olive oil, coffee and tea can also be analyzed as described herein. In addition, biological compositions, such as growth media and vaccines, and explosive, flammable, or otherwise hazardous substances can be assessed with the methods of the invention.

As described in more detail below, the present methods can be performed on sealed containers, e.g., without violating the seal on the container, e.g., a label, cork, screw top, or other closure mechanism. In preferred embodiments, the sealed containers are intact wine bottles, but these methods are equally applicable to other sealed containers, e.g., those containing consumables or other liquids, solids, gels, powders, or the like, for which contamination, degradation, potential hazard or authenticity are of interest.

Containers and Substances for Analysis

Before describing the present invention in detail, it is to be understood that this invention is not limited to particular devices or container systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "an electrode" includes a combination of two or more electrodes; reference to a "coil" includes mixtures or series of coils, and the like.

Unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein. In describing and claiming the present invention, the following terminology will be used in accordance with the definitions set out below.

The term "sealed container" refers to a packaged or unopened vessel or receptacle, e.g., one containing consumables such as wine, brandy, cognac or the like. The present invention provides methods of analyzing one or more contents of a sealed container. The sealed container can be any of a number of food or beverage containers having contents of interest, including, but not limited to, alcoholic and/or nonalcoholic beverages. Other containers containing growth media or biological solutions, blood, vaccines, drugs, bioterrorism or potentially explosive agents can also be analyzed using the methods of the inventions.

A sealed container for use with the methods and devices of the invention can be made of either clear or colored (e.g., amber, green or brown) glass or any other nonconductive material, e.g., plastic, ceramic, porcelain, or wood. Preferably, the containers analyzed are glass, e.g., wine bottles. In addition, a beeswax seal and/or lead cap, often used in the corking or sealing process, or any other type of 11d or closure need not be removed for the analysis. The coils and probes described herein can also be positioned and/or fabricated to be used with other containers of interest, e.g., water bottles, cans, or the like.

In a preferred embodiment, the container is a corked (e.g., unopened) bottle of wine. Any number of wine bottle "styles" can be accommodated in the methods (as well as devices and systems) of the present invention. For example, the methods of the present invention can be used to analyzed the contents of the high shouldered "Bordeaux" bottle (typically used for Sauvignon Blanc, Cabernet Sauvignon, Merlot, and Bordeaux blends), the slope shouldered "Burgundy" bottle (Chardonnay and Pinot Noir), or the taller "Hoch" bottle of Germanic origin (Rieslings and Gewurztraminers). The contents of champagne/sparkling wine bottles, Chianti bottles, and the shaped-neck bottles typically used for fortified wines (port, sherry, etc.) can also be analyzed by the methods of the present invention. Furthermore, a range of bottle sizes and shapes can be used in the methods of the present invention; in addition to the 750 mL bottle found in typical wine cellars, the smaller half bottles, "splits" (187 mL) and "tenths" (375 mL) as well as the larger "magnum" bottles (e.g., 1 L, 1.5 L and 3 L bottles) can be examined.

In addition to wine, other consumables can be analyzed by the methods of the present invention, including, but not limited to, brandy, cognac, beer, vinegar, and olive oil. In addition, sealed receptacles containing solutions or suspensions not typically considered as "food" (e.g., microbial culture media, herbal tinctures, and the like) can also be examined using the methods of the present invention. Non-consummables, such as liquids thought to contain infectious matter, poison, pathogens, acids, or explosive material can also be analyzed using the methods of the invention. Preferably, the component of interest in the sealed container generates a dielectric absorption response or magnetic susceptibility to an applied electric or magnetic field as described in more detail below.

Dielectric Absorption

Different substances, e.g., different types or vintages of wine, different blood samples, vaccines, or explosives, have a unique set of electrical characteristics that are dependent on the dielectric properties of the substance. Dielectric spectroscopy (also called impedance spectroscopy) measures the dielectric properties of a substance as a function of frequency. It is based on the interaction of an external field with the electrical susceptibility of the sample. In dielectric spectroscopy the current flowing through a sample and the voltage across the sample are measured as a function of frequency. From this data one can obtain the impedance of the solution as a function of frequency. When subjected to statistical analysis as described below, a fingerprint of a substance such as wine can be determined from the spectra produced from dielectric spectroscopy. Any substance, including liquids, solids, gels, and gases, that exhibits dielectric properties can be analyzed using the methods of the invention.

The dielectric absorption apparatus shown in FIG. 1 uses bottom ring electrode 110 to measure the amplitude and phase of the dielectric current J(t) in sealed container 100, e.g., a wine bottle, established by a frequency swept electric field (applied by waveform generator 140 in FIG. 1)

$$\overline{E}(t) = \overline{E}_0 \cos(\omega_{app} t) \qquad \text{Equation 1}$$

with amplitude $E_0$ and applied frequency $\hat{\omega}_{app}$, e.g., established by top ring electrode 105. The dielectric displacement D(t) due to the wine bottle contents (The use of annular electrodes avoids bottle dependent responses) develops in response to the applied electric field in Eq. (1) as $$\overline{D}(t) = \overline{D}_0(t) + \overline{P}(t) = \in_0 \overline{E}(t) + \chi(t) \overline{E}_0 \qquad \text{Equation 2}$$

where $D_0(t) = \in_0 E(t)$ and $P(t) = \chi(t) E_0$ respectively correspond to the through space and medium polarization contributions to the dielectric displacement D(t), $\in_0$ is the permittivity of free space, and χ(t) is the scalar part of the frequency dependent electric susceptibility that can be expressed in terms of the in phase χ(ω)' and quadrature out of phase χ(ω)" components in the usual way as $$\chi(t)=\chi(\omega_{app})' \cos(\omega_{app}t)+\chi(\omega_{app})'' \sin(\omega_{app}t). \quad \text{Equation 3}$$

Inserting Eqs. (1) and (3) into Eq. (2) allows the time derivative of the dielectric displacement, the dielectric current J(t) that is monitored by the bottom ring electrode shown in FIG. 1, to be determined as $$\bar{J}(t) = \frac{d}{dt}\bar{D}(t) \quad \text{Equation 4}$$
$$= \omega_{app}\bar{E}_0 \begin{pmatrix} \chi(\omega_{app})''\cos(\omega_{app}t) - \\ (\chi(\omega_{app})' + \varepsilon_0)\sin(\omega_{app}t) \end{pmatrix}.$$

It is the frequency dependent variation of the amplitude and phase of the developed current in this equation versus the amplitude and phase of the applied electric field in Eq. (1) that become inputs for PCA in this study. The Fourier transform of the applied electric field $E(\omega)=E_0\delta(\omega-\omega_{app})$ and the induced dielectric current $$\bar{J}(\omega)=\omega\bar{E}_0(\chi(\omega)''-i(\chi(\omega)'+\varepsilon_0))\delta(\omega-\omega_{app}) \quad \text{Equation 5}$$

are used to construct the electric field amplitude attenuation A from a ratio of the magnitude of Eq. (5) to the magnitude of the Fourier transform of Eq. (1) as $$A = \frac{\|\bar{J}(\omega)\|}{\|\bar{E}(\omega)\|} = \omega(\chi(\omega)'^2 + (\chi(\omega)' + \varepsilon_0)^2)^{1/2} \quad \text{Equation 6}$$

and to develop the phase retardation Φ from a ratio of the imaginary and real parts of Eq. (5) as $$\phi = \phi_{sig} - \phi_{ref} = a\tan\left(\frac{\chi(\omega)' + \varepsilon_0}{\chi(\omega)''}\right) \quad \text{Equation 7}$$

where φref=0 for the simple case of an applied monochromatic electric field described by Eq. (1).

Magnetic Susceptibility

Figure 5A:
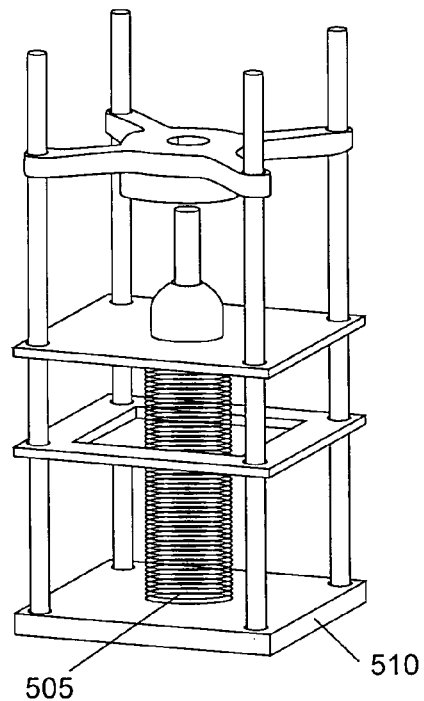
FIG. 5a shows structure 510 with coil (or solenoid) 505, into which a container can be placed.
Figure 5B:
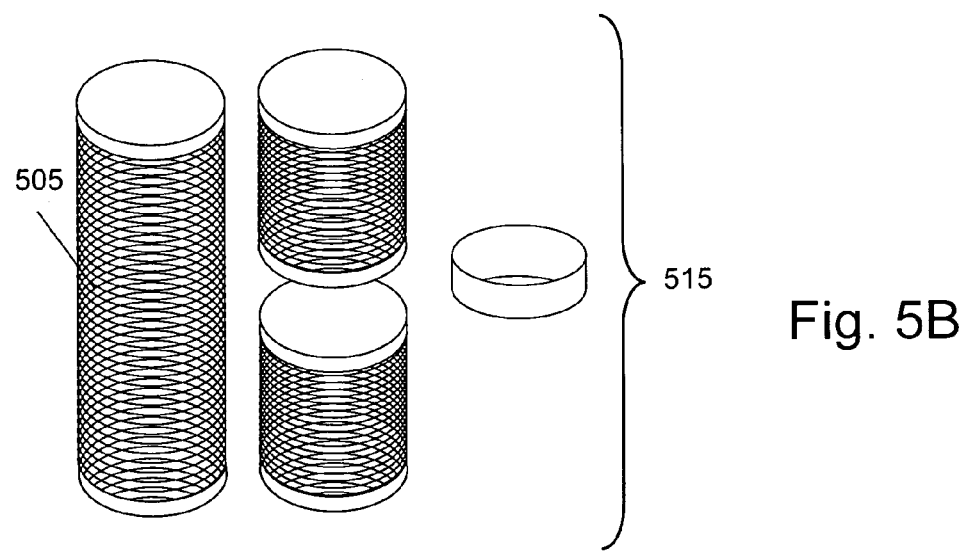
FIG. 5b illustrates primary solenoid coil 510 and secondary coil 515 which can be mounted inside of coil 510. A container of interest can be placed in the probe without opening or unsealing it in any way, thereby allowing a non-invasive analysis of the components.
Figure 6A:
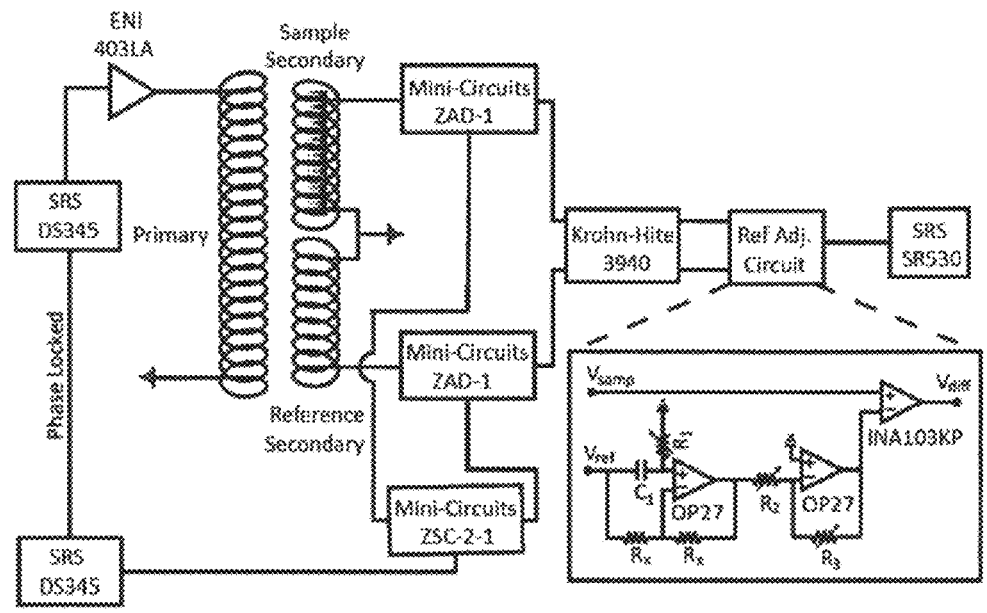
FIG. 6A illustrates a system for applying a magnetic field to a container and monitoring an effect on the magnetic field.
Figure 6B:
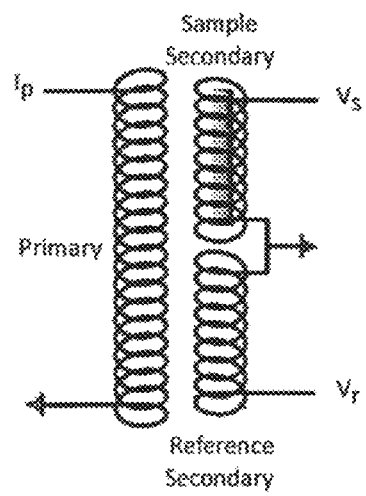
FIG. 6b illustrates the secondary coil as a gradiometer with sample coil and reference coil, both of which are mounted inside of the primary coil.

Direct magnetic field coupling between the primary and the sample secondary coils shown in FIGS. 5 and 6 is the dominant source of induced voltage and therefore signal in the mutual inductor setup. It is the small perturbation to this direct coupling that is observed when a sample is added to one half of the sample secondary as shown in FIG. 6. Choosing to operate the sample secondary in gradiometer mode physically limits the induced voltage due to direct coupling so that the measured voltage $V_s$ is strictly due to the induced magnetization of the sample or more specifically the complex magnetic susceptibility of the sample.

The voltage measured from the secondary coil $V_s$ shown in FIGS. 5 and 6 is related to the current applied to the primary coil $I_p$ and more importantly the magnetic susceptibility χ of the sample. In the case of an applied DC current $I_p$ the applied magnetic field inside of the primary coil is $$H = \frac{nI_p\pi r_p^2 b}{\ell} \quad (1)$$

where $n_p$ is the number of turns in the primary coil, lp is the length of the primary coil, $r_p$ is the radius of the primary coil, and b is an empirical correction factor. In the absence of any sample inside of the primary coil the magnetic induction B is $$B=\mu_0 H \quad (2)$$

where the proportionality of $\mu_0$ is the permeability of free space. When a sample is placed inside of the primary coil described with a magnetic susceptibility χ the magnetization $$M=\chi H \quad (3)$$

develops and adds to the applied magnetic field H to change the magnetic induction to $$B=\mu_0(H+M)=\mu_0 H(1+\chi) \quad (4)$$

in the usual way. In the case where paramagnetic substances are used χ>0 and an increase in the magnetic induction is observed while for diamagnetic samples the magnetic induction decreases as χ<0.

The steps leading to the fundamental magnetostatic result shown in Eq. (4) were included here as they directly apply to the actual experiment performed in this work involving an applied AC current to the primary coil where $$I_p(t)=I_0\cos(\omega t) \quad (5)$$

and $$H(t)=H_0\cos(\omega t) \quad (6)$$

with $H_0=nI_0r_p^2 b/l$. As in the magnetostatic case shown in Eq. (2) in the absence of any sample, the applied time dependent field translates into the time dependent magnetic induction $$B=\mu_0 H_0 \cos(\omega t). \quad (7)$$

In parallel with an applied DC field, introduction of a sample to the primary coil leads to the creation of magnetization, however in the case of an applied AC field both an amplitude attenuation and a phase retardation of the applied time dependent field H(t) is observed. In this case the sample magnetization can be described as $$M(t)=H_0[\chi'(\omega)\cos(\omega t)+\chi''(\omega)\sin(\omega t)] \quad (8)$$

where the in-phase dissipative and the quadrature out-of-phase dispersive frequency and sample dependent components of the magnetic susceptibility are given by χ'(ω) and χ"(ω) respectively and the magnetic induction becomes $$B(t)=H_0[(\mu_0+\chi'(\omega))\cos(\omega t)+\chi''(\omega)\sin(\omega t)]. \quad (9)$$

It is the magnetic induction produced by the applied time dependent magnetic field H(t) shown in Eq. (9) that leads to a measurable voltage $V_s=V_r$ from the gradiometer coil shown in FIG. 6(b) that is mounted inside of the primary coil shown in FIG. 5(a). The sample voltage $V_s$ is generated from the top half of the gradiometer coil containing the sample shown in FIG. 6(b) while the reference voltage $V_r$ is produced from the sample-free counter wound lower half of the gradiometer coil shown in FIG. 6(b). It should be clear that in the absence of any sample in the optimum situation (never observed) that the primary coil produces the same field inside of both halves of the gradiometer forcing $V_s=V_r$ and thus the measured signal $V_s-V_r$ to zero. This result, as well as the more applicable case where a sample is contained within the top half of the gradiometer coil with cross sectional area $A_g$ and number of turns $n_g/2$, can be determined from Faraday's law of induction as $$V_s = \frac{n_g}{2}\frac{d}{dt}\int B(t)\cdot dA \qquad (10)$$

$$= \frac{n_g A_g H_0 \omega}{2}[(\mu_0 + \chi'(\omega))\sin(\omega t) - \chi''(\omega)\cos(\omega t)]$$

for the sample-loaded half of the gradiometer coil and $$V_r = \frac{n_g}{2}\frac{d}{dt}\int B(t)\cdot dA \qquad (11)$$

$$= \frac{n_g A_g H_0 \omega}{2}\mu_0\sin(\omega t)$$

for the sample-free reference half of the gradiometer. The measured difference voltage $$V_s - V_r = \frac{n_g A_g H_0 \omega}{2}(\chi'(\omega)\sin(\omega t) - \chi''(\omega)\cos(\omega t)) \qquad (12)$$

naturally cancels the unwanted direct coupling effect between the primary and secondary coils because the separate halves of the gradiometer are counter-wound with respect to each other. Consequently the overall dynamic range dramatically improves and in the perfectly balanced gradiometer situation (never realized) corresponds to a background free experiment. Equation (12) can be rewritten as $$V_s - V_r = \frac{n_g A_g H_0 \omega}{2}\sqrt{\chi'(\omega)^2 + \chi''(\omega)^2}\cos\left[\omega t + \mathrm{atan}\left(\frac{\chi''(\omega)}{\chi'(\omega)}\right)\right] \qquad (13)$$

where the relationship between the measured amplitude $$A(\omega) = \frac{n_g A_g H_0 \omega}{2}\sqrt{\chi'(\omega)^2 + \chi''(\omega)^2} \qquad (14)$$

and phase $$\phi(\omega) = \mathrm{atan}\left(\frac{\chi''(\omega)}{\chi'(\omega)}\right) \qquad (15)$$

to material parameters $\chi'(\omega)$ and $\chi''(\omega)$ as a function of frequency $\omega$ establish a fingerprint for a particular sample.

The description provided above is appropriate for a situation where the gradiometer setup is perfectly balanced. To ensure that the measured voltage difference $V_s$–$V_r$ results from sample induced magnetization rather than coil symmetry imperfections each half of the gradiometer coil must be meticulously matched in both observed field (physical position in the primary) and physical dimensions (inner/outer diameter, length and number of turns). While in the manufacturing of the mutual inductor setup extreme care was taken to match both halves of the gradiometer as well as gradiometer position inside of the solenoid primary, in actuality the measured voltage difference $V_s$–$V_r$ was never zero even in the absence of sample in the top half of the gradiometer. This observation is to be expected as the frequencies considered in this study are well above the self resonant frequencies of the coils thus making the voltage drop in the primary coil a strong function of position and frequency, an effect that leads to a gradiometer coil with unbalanced outputs $V_s$ and $V_r$. In order to compensate for this effect the balance circuit shown in FIG. 6(a) was constructed with added electronics hardware that dramatically improves measurement sensitivity to sample solutes by allowing the effects of container and solvent to be removed from the $V_s$–$V_r$ signal.

For further review of magnetic susceptibility, see, e.g., Juri, L. O.; Bekeris, V. I.; Steinmann, R. G., Skin Depth and Complex Magnetic Susceptibility: An Experimental Alternative Approach. *American Journal of Physics* 1985, 54, (9), 836-838; Kuipers, B. W. M.; Bakelaar, I. A.; Klokkenburg, M.; Erne, B. E., Complex Magnetic Susceptibility Setup for Spectroscopy in the Extremely Low-Frequency Range. *Review of Scientific Instruments* 2008, 79, 013901; Maxwell, E., Mutual Inductance Bridge for ac Susceptibility Measurements at Low Frequencies. *Review of Scientific Instruments* 1964, 36, 553-554; and Schmitz, T.; Wong, M. *Choosing and Using Bypass Capacitors;* 2007.

Principal Component Analysis

Principal component analysis (PCA) is a statistical method that transforms a number of possibly correlated variables into a smaller number of uncorrelated variables called principal components. The central idea of principal component analysis (PCA) is to reduce the dimensionality of a data set consisting of a large number of interrelated variables, while retaining as much as possible of the variation present in the data set. This is achieved by transforming to a new set of variables, the principal components (PCs), which are uncorrelated and are ordered so that the first few retain most of the variation present in all of the original variables.

PCA transforms n measurements e.g. pressure, volume, temperature, spectral data point, etc. for a large number of samples m organized into a set of m n×1 column vectors $d_q$ as $$\vec{D}_q = \tilde{S}\cdot\vec{d}_q \qquad \text{Equation 8}$$

where the index q pertains to one of the m samples, $D_q$ is the transformed data vector, and the unitary transformation matrix S is constructed from a knowledge of the variance of the nth measurement and the covariances of the n measurements included in the m different samples. Gathering the m n×1 measured data records for the m samples $d_q$ into an n×m data matrix d with the matrix elements:

$$\hat{k}^\dagger\cdot\tilde{d}\cdot\hat{q} = \hat{k}^\dagger\cdot\vec{d}_q - \sum_{j=1}^{m}\frac{\hat{k}^\dagger\cdot\vec{d}_j}{m} \qquad \text{Equation 9}$$

allows Eq. (8) to be rewritten as $$\tilde{D} = \tilde{S}\cdot\tilde{d} \qquad \text{Equation 10}$$

where the matrix elements of the n×m transformed data matrix D are related to the n elements of the transformed data vector $D_q$ as $$\hat{k}^\dagger\cdot\tilde{D}\cdot\hat{q} = \hat{k}^\dagger\cdot\vec{D}_q - \sum_{j=1}^{m}\frac{\hat{k}^\dagger\cdot\vec{D}_j}{m}. \qquad \text{Equation 11}$$

The last term on the right hand side of Eq. (9) is the average across the m samples for the $k^{th}$ measurement, a mean that transforms to the last term on the right in Eq. (11). Representation of the measured and transformed data in terms of the respective d and D matrices allows the n×n covariance of the transformed data cov{D}=D† to be related to the n×n covariance of the measured data cov{d}=d d† as $$\text{cov}\{\tilde{D}\}=\tilde{S}\cdot\text{cov}\{\tilde{d}\}\cdot\tilde{S}^{\dagger}$$ Equation 12 using Eq. (8) and the fact that matrix multiplication is associative. In PCA the transformation matrix S is chosen so that the matrix cov{D} is diagonal. It should be clear that the matrix elements of cov{D} are the eigenvalues $\lambda_k$ of the matrix cov{d} while the columns of the adjoint transformation matrix S† are the corresponding eigenvectors or principal components $P_k$. Indeed since n measurements have been considered there will be n eigenvalues $\lambda_k$ and n eigenvectors $P_k$. The eigenvector corresponding to the largest eigenvalue is the first principal component $P_1$, the eigenvector for the second largest eigenvalue is the second principal component $P_2$, and so on. In most cases where PCA is applied, greater than 95% of the total variance in the measured data is contained within the first two principal components, vectors that can be used to reduce multidimensional data to fewer dimensions. The projection of the measured data on the first principal component $P_1$ as $$x_q=\overline{P}_1^{\dagger}\cdot\overline{d}_q$$ Equation 13 and on the second principal component $P_2$ as $$y_q=\overline{P}_2^{\dagger}\cdot\overline{d}_q$$ Equation 14

Although the preferred embodiment of the invention uses principal component analysis to interpret the data, other statistical methods can optionally be applied, e.g., Multivariate Least Squares Regression, Principal Component Regression, Pattern Recognition analysis, Cluster analysis, and/or Neural Net analysis.

Methods of the Invention

The invention provides methods of analyzing sealed containers, e.g., unopened or intact bottles of wine, beer, vinegar, olive oil, water, ink, blood, or the like. The containers can be analyzed for purity, authenticity, potential hazard, or the like. For example, a spectrometer is coupled to a probe, e.g., a coil, set of coils, or an electrode, that surrounds the sealed container of interest and applies an electric or magnetic field to the container and its contents. In one preferred embodiment, the methods are used to analyze a wine bottle by detecting the dielectric displacement of an applied electric field via annular electrodes in contact with the bottle. In another embodiment, a waveform generator applies a frequency swept electric field to a solenoid coil or set thereof surrounding the container thereby producing a magnetic field. Any change in the magnetic field due to contents of the container is detected and used to develop a magnetic susceptibility fingerprint or profile of the contents of the container.

The responses detected, e.g., perturbations in the electric or magnetic field due to the contents of the container, are typically transferred to a software system such as Matlab for data processing, e.g., to produce Fourier Transformed absorption spectra. The data are then typically interpreted according to a statistical technique, such as Principal Component Analysis (PCA) which is a preferred method. The end result of the data analysis provides a dielectric signature or fingerprint of the contents of the container. The fingerprint for a test substance is compared to a fingerprint or profile for a calibration substance to determine whether the two fluids are the same.

In one embodiment, the use of annular or circular electrodes allows the effects of the container, e.g., bottle thickness and glass content variations around the container circumference, on the measured signal to be minimized as long as an electrode separation is maintained. As a comparison, the use of more standard parallel plate electrodes yields signals that are more strongly container dependent instead of container contents dependent.

This embodiment typically comprises applying a frequency swept electric field to a first annular electrode surrounding a first portion of a container, e.g., a wine bottle; and detecting a response, e.g., dielectric absorption, at a second annular electrode, which second annular electrode surrounds a second portion of the container. Principal component analysis (or another statistical method) is then used to develop a dielectric signature or fingerprint of the contents of the container.

The responses detected, e.g., at the second electrode, are typically in the form of signal attenuation or phase retardation as a function of frequency, e.g., from about 200 Hz to about 24 MHz. For example, the various components of wine and the concentration of each cause different wines to affect the applied electric field in a different manner, thereby allowing differences to be identified.

Another embodiment provides a method of authenticating a test sample compared to a known sample, comprising monitoring changes in an applied electric field between two electrodes as the electric field travels through a medium, wherein the first and second annular electrodes are positioned around a known bottle of wine, thereby producing a first dielectric profile. The same analysis is also performed on the test bottle, e.g., by applying an identical electric field at a first electrode and monitoring the effects on that electric field at a second annular electrode, which electrodes are positioned around a test bottle of wine thereby producing a second dielectric profile. The method compares the first dielectric profile and the second dielectric profile, thereby determining if the test bottle of wine is the same as the known bottle of wine. In the same manner, a container of interest, e.g., one suspected of containing illegal and/or hazardous substances, can be compared to one known to have safe and/or pure contents to determine a potential hazard level or to indicate whether the contents have been tampered with or otherwise contaminated.

For example, the methods herein can be used to authenticate a bottle of wine, e.g., compare one bottle, e.g., of a rare wine or brandy, to a known bottle of the same vintage. The methods of the invention typically combine a simple apparatus, e.g., as shown in FIG. 1, with principal component analysis (PCA). (Jolliffe, I. I., *Principal Component Analysis*. 2nd ed.; Springer: Berlin, 2002.) Briefly, a commercial-off-the-shelf waveform or function generator is used to broadcast a frequency swept electric field across the sealed container, e.g., across a wine bottle length, via an annular electrode such as ring electrode 105 around sealed container 100 in FIG. 1 (shown in FIG. 1 as a thick horizontal line below the wine bottle shoulder). Dielectric responses from the contents of the sealed container attenuate the amplitude and retard the phase of the applied electric field (Kremer, F.; Schonhals, A., *Broadband Dielectric Spectroscopy*. Springer: Berlin, 2003). These effects can be detected by a second annular or ring electrode, e.g., electrode 110 in FIG. 1 (shown as a thick horizontal line at the base of the wine bottle). Application of this method to several standard solutions of ethyl alcohol, acetic acid, potassium sulfate, and glycerol in de-ionized water with concentrations chosen to bracket the expected average concentration in wine (Pohl, P., What do Metals Tell us about Wine? *Trends in Analytical Chemistry* 2007, 26, (9), 941-949; Noble, A. C.; Bursick, G. F., The Contribution of Glycerol to Perceived Viscosity and Sweetness in White Wine. *American Journal of Enology and Viticulture* 1984, 35, (2); Crowell, E. A.; Ough, C. S., A Modified Procedure for Alcohol Determination by Dichromate Oxidation. *American Journal of Enology and Viticulture* 1978, 30, (1), 61-64; Joyeux, A.; Lafon-Lafourcade, S.; Riberequ-Gayon, P., Evolution of Acetic Acid Bacteria During Fermentation and Storage of Wine. *Applied and Environmental Microbiology* 1984, 48, (1), 153-156.) indicates that different electric field frequencies can probe different constituents in wine. As the concentration of each of these solutes, in addition to the numerous other wine compounds such as tannins and flavenoids, are specific to each wine; the frequency dependent electric field amplitude attenuation and phase retardation can be used in combination with PCA to group like wine vintages and thus fingerprint wine. Comparison of the dielectric absorption of a potential counterfeit bottle response to that of a known authentic wine can be used to verify the contents of a sealed container, e.g., a suspected counterfeit bottle of wine, brandy, cognac, or other substance.

In other embodiments, the present invention can be used to identify contaminants, e.g., acetic acid, in a sealed container, e.g., by comparing to a fingerprint of material that is known to be uncontaminated or by identifying an unusual component, e.g., one that is illegal, hazardous or otherwise undesirable, present in the container through an unusual dielectric response. This too can be done as described herein without breaking, opening, or otherwise violating or disrupting the seal on the container.

In another preferred embodiment, a solenoid probe is used. When the frequency swept electric field is applied to the solenoid coil, e.g., one into which a wine bottle or other container can be positioned, it generates a magnetic field. Frequencies from about 500 Hz to about 30 MHZ are typically used in this embodiment. Changes in the magnetic field are detected via a set of inner solenoid coils, e.g., a sample coil and a reference coil as illustrated in FIGS. 5 and 6. This embodiment is also useful for the authentication of wine as described above.

Devices and Systems of the Invention

The invention also provides devices and systems for analyzing a sealed container, e.g., a container comprising a fluid such as wine, vinegar, olive oil, beer, brandy, cognac, or the like. The devices used to analyze the contents of a sealed container do so without breaking or compromising the seal in any way. Furthermore, the devices do not alter, e.g., destroy, the contents of the container. Therefore, the invention provides a non-destructive, non-invasive apparatus for determining or verifying the contents of sealed containers, e.g., to authenticate a rare bottle of wine.

Containers that can be analyzed or authenticated with the devices and methods of the systems are typically made of glass or another non-conductive substance, e.g., plastic. The container can be any size and shape capable of having an electrode affixed so that it surrounds the container or that can be fitted within the solenoid feature of the magnetic embodiment.

The devices of the invention typically comprise a waveform generator, e.g., a sinusoidal function generator such as an Agilent 33250A, function/arbitrary waveform generator. The waveform generator is operably coupled to a probe, e.g., an electrode, that encircles and contacts the container and applies an electric field thereto, e.g., a swept frequency electric field. Electrodes can be affixed temporarily to the bottle, e.g., using tape, hook and loop fasteners, or other adhesives, so that both the device and the electrodes can be reused. Alternatively, a support structure can be constructed to which the electrodes are attached. The sealed contained can then be positioned therein for analysis.

The electrode is typically a circular ring of copper, but can alternately be a coil that encircles the length of the container. Although copper has been used to generate the data presented herein, other electrically conductive less malleable metals like beryllium/copper alloy can be used. Coupling of the electric field into the wine bottle with circular electrode straps is superb, even if they are manually wrapped around the bottle for each measurement.

An alternative probe for generating a magnetic susceptibility fingerprint or profile is a solenoid probe, e.g., into which a wine bottle can be placed. This provides an easy to reuse system into which various containers can be placed and removed and replaced. See, e.g., structure 510 and solenoid 505 in FIG. 5a. In this embodiment, an outer or primary solenoid coil is provided, into which an rf waveform is applied, thereby generating a magnetic field. At least two inner solenoids are also typically used, e.g., as described in more detail in the example section below. The inner or secondary solenoids include a sample coil and a reference coil. The container is placed within the sample coil and the coils are arranged and the fields manipulated such that any container dependent effects are eliminated from the resulting data set. This is described in more detail in the magnetic susceptibility section above and shown in FIG. 6.

Additional components of the devices of the system can include, but are not limited to, a power splitter, an oscilloscope, an amplifier, a receiver, a detector, and a computer. A power splitter is used, e.g., to split a waveform into two sinusoidal waves—a reference and an input signal. An amplifier is used to amplify a signal, e.g., an output signal from the second electrode, e.g., electrode 110. In a preferred embodiment a transimpedance amplifier is used. An oscilloscope is typically used to digitize an analog signal and is also optionally used to display the data, which is then typically transferred to a computer for data processing, e.g., Fourier transforming and PCA to produce the dielectric fingerprint profiles of the substance in the container.

The present invention also provides integrated systems for analyzing contents of a sealed container. The systems include an electric field generator, e.g., a waveform generator that applies an electric field to an annular probe, e.g., two circular electrodes that surround the container in two different positions or a coil that surrounds the container, and a receiver system configured for electronic communication with the probe. Optionally, the receiver system and the field generator are incorporated into the same body structure to form a portable spectrometer. The receiver system also typically comprises a power splitter and an amplifier and a computer configured for coupling to the probe and receiving and analyzing the signal, e.g., from the second electrode. The probes and systems of the present invention can be used to perform dielectric or diamagnetic spectroscopy on sealed containers made from non conductive materials and containing substances that exhibit dielectric or diamagnetic properties.

Systems of the invention can also include statistical analysis software to interpret signal or response data, e.g., to perform PCA on the frequency dependent responses detected at a sample container after an applied electric or magnetic field. For example, many vendors, such as Partek Incorporated (St. Peters, Mo.; www.partek.com) provide software for pattern recognition which can be applied to signal interpretation and analysis. Relationships between datasets (can similarly be analyzed, e.g., by pattern recognition software, Bayes classifiers, neural networks, Monte Carlo analysis, Principal Component Analysis (PCA), Markov modeling, etc. Computers/digital appliances also optionally included or are operably coupled to user viewable display systems (monitors, CRTs, printouts, etc.), printers to print data relating to signal information, peripherals such as magnetic or optical storage drives, user input devices (keyboards, microphones, pointing devices) and the like.

A schematic diagram of an exemplary system of the invention is provided in FIG. 1. Waveform generator 140 produces a waveform that is split by splitter 130, which input is divided into two channels in oscilloscope 150. One channel receives a reference signal and the other receives the test signal that has been applied to bottle 100 through electrode 105 and received or detected at electrode 110 and amplified by transimpedance amplifier 120. The data are then transferred to computer 160 for data analysis.

A kit comprising a probe, a waveform generator, a receiver, and/or one or more standard, e.g., pure, solutions is also an embodiment of the invention. For example, a kit optionally contains e.g., standard solutions of contaminants (e.g., acetic acid titration samples) or a standard solution of any substance of interest in a sealed container, for use in the methods, devices or systems of the present invention. Optionally, the kit further comprises an instruction manual for performing the methods and analysis of the present invention.

EXAMPLES

The following are examples illustrate the methods and systems of the invention, e.g., analyzing the contents of sealed containers based on electric or magnetic susceptibility with PCA applied to the results. It will be appreciated that such descriptions and examples are not necessarily limiting upon the methods, devices, systems, etc., of the invention. It is understood that examples and embodiments described herein are for illustrative purposes only and that various modifications or changes in light thereof will be suggested to persons skilled in the art and are to be included within the spirit and purview of this application and within the scope of the appended claims.

Example 1

Methods for Authenticating Full Intact Wine Bottles Based on Dielectric Fingerprinting Experimental Details All chemicals were obtained from Sigma-Aldrich and used without further purification. Sixteen bottles of CHARLES SHAW wine obtained from TRADER JOE'S were drained, cleaned, and refilled with solutions of deionized water and ethyl alcohol, acetic acid, potassium sulfate, glycerol, and sucrose. One bottle filled with deionized water served as a standard solution while the remaining fifteen were filled with five sets of three solutions of each of these compounds as described in Table 1.

TABLE 1

Solution Sample Set

| | Concentration | | | |
|---|---|---|---|---|
| Solute | Sample 1 | Sample 2 | Sample 3 | Sensitivity |
| ethyl alcohol | 20.00 ± 0.01% (v/v) | 13.00 ± 0.01% (v/v) | 5.00 ± 0.01% (v/v) | 2,357 ± 23 |
| acetic acid | 3.75 ± 0.05 mL/L | 2.25 ± 0.05 mL/L | 0.375 ± 0.05 mL/L | 3,261 ± 9 |
| potassium sulfate | 2.39 ± 0.01 g/L | 0.747 ± 0.01 g/L | 0.253 ± 0.01 g/L | 8623 ± 15 |
| glycerol | 19.78 ± 0.01 g/L | 10.00 ± 0.01 g/L | 4.02 ± 0.01 g/L | 523 ± 2 |
| sucrose | 33.75 ± 0.01 g/L | 15.00 ± 0.01 g/L | 6.01 ± 0.01 g/L | — |

The solution concentrations were chosen to bracket the mean amounts reported for wine.

Six sets of two duplicate bottles of the 1990 GRAND VIN DE CHATEAU LATOUR, the 1958 GRAND VIN DE CHATEAU LATOUR, the 2002 OPUS ONE, the 1985 OPUS ONE, the 1994 Petrus Pomerol, and the 1979 Petrus Pomerol were used to construct a wine authentication library.

The spectrometer shown in FIG. 1 was used to measure the room temperature dielectric properties of the prepared full bottle solutions and the collectible wine in the 200 Hz to 24 MHz frequency range. The output of a Stanford Instruments SRS DS345 function generator was split into two frequency swept sinusoidal waveforms with a BNC T below $v=24$ kHz and with a Minicircuits ZSC-2-1 splitter above $v=150$ kHz. One waveform was directed into channel 1 of a Tektronix 724D 2 GS/s digital oscilloscope to serve as an amplitude and phase reference while the other waveform was directed into a 1.3 cm wide 50 µm thick copper strap wrapped around the upper portion of a wine bottle as shown in FIG. 1. In this way the thin copper ring served as a broadcast antenna to couple the waveform into the wine bottle. An identical thin copper detection ring mounted 10.2 cm below the broadcast ring was used to receive the oscillating field. A LM6624MA op-amp based transimpedance amplifier converted the induced current into voltage and coupled the weak signal into channel 2 of the Tektronix oscilloscope. Signal averaging, Tektronix oscilloscope control, and SRS DS345 function generator control was accomplished with a National Instruments NI PCI-GPIB card.

Electrical absorption spectra for full wine bottles in the 200 Hz<$v$<24 MHz frequency range were obtained in two blocks chosen based on the performance of the frequency splitter shown in FIG. 1. Each frequency block used the same 9.5 V peak-to-peak output voltage from the SRS DS345 function generator with a $2.4\times10^{-3}$ kHz$^2$ frequency sweep rate in the 200 Hz<$v$<24 kHz range and a $23.9\times10^{-3}$ MHz$^2$ frequency sweep rate in the 150 kHz<$v$<24 MHz range. Twenty acquisitions of fifty thousand points were acquired for both the reference (channel 1) and sample response (channel 2) signals for each of these frequency ranges and were uploaded to Matlab via the GPIB connection where they were averaged. All measurements were accomplished at room temperature, 20° C.

All data processing was accomplished with Matlab. The 50,000 point, 20 scan averaged signals for the reference (channel 1) and absorption (channel 2) were Fourier transformed in order to obtain the amount of electrical absorption and phase change at each frequency. The frequency domain absorption signal corresponds to a ratio of the magnitude of the Fourier transformed absorption spectrum to the reference spectrum as prescribed by Eq. (6). The frequency dependent relative phase between the reference and absorption signal was obtained by comparison of the respective complex Fourier transformed data as dictated by Eq. (7). The resulting absolute value and phase dependent spectra for each of the frequency bands were truncated to the appropriate sweep bandwidth 200 Hz<v<24 kHz or 150 kHz<v<24 MHz as the Fourier transform bandwidth pertains to the inverse dwell time between each of the 50,000 data points, a number much greater than the actual sweep bandwidth applied with the SRS DS345 function generator. A five point progressive frequency average was used to smooth each of the Fourier transformed spectra and 80,000 of the overall 100,000 measured points for each bottle corresponding to the least noisy regions of these spectra were treated with PCA as described in the last section.

Results

The dielectric absorption for each of the samples shown in Table 1 was obtained in the 200 Hz<v<24 MHz frequency range using the apparatus shown in FIG. 1 as described in the Experimental section. The amplitude attenuation and phase retardation of the input frequency swept waveform due to dielectric absorption for the three separate solution concentrations for each solute along with the same data for the pure solvent de-ionized water was used to construct a sample library. In this way five separate four sample libraries were created to demonstrate the solution dependence of the dielectric absorption of specific wine constituents. FIG. 2 shows the first principal component obtained in the 200 Hz<v<24 kHz frequency range based on the amplitude attenuation (a) and phase retardation (b) of the measured waveforms corresponding to the glycerol (solid line), ethyl alcohol (long dashed line), potassium sulfate (short dashed line), and acetic acid (long/short dashed line) libraries. The first principal components for these same libraries based on the amplitude attenuation (a) and phase retardation (b) of the measured waveform in the 150 kHz<v<24 MHz scan region are shown in FIG. 3. As the measured amplitude attenuation and phase retardation in the sucrose solutions was independent of concentration across both of these frequency bands, data for the sucrose solutions was not included in FIGS. 2 and 3. For all of the measurements shown in FIGS. 2 and 3, ca. 94% of the library variance is included in the first principal component $P_1$. The right hand column in Table 1 corresponds to the sensitivity of the method to expected natural solute concentrations, a number that is determined from the slope of the $x_q$ values as a function of concentration for each solute library.

The dielectric absorption for the twelve collectible wines was obtained in the 200 Hz<v<24 MHz frequency range in two blocks as described in the Experimental section. The amplitude attenuation and phase retardation of the applied frequency swept waveform for each bottle was used to construct a library. Principal component analysis followed by projection of the amplitude attenuation and phase retardation data for a given bottle onto the first two principal components with Eqs. (13) and (14) yields the $x_q$ and $y_q$ coordinate values for each bottle shown in the plot in FIG. 4. Here the closed and open squares correspond to the 1985 and the 2002 vintages of OPUS ONE respectively, the closed and open lozenges correspond to the 1958 and 1990 vintages of GRAND VIN DE CHATEAU LATOUR respectively, and the closed and open triangles correspond to the 1979 and 1994 vintages of Petrus Pomerol respectively. In this case, the percentage of the total variance captured by projecting the measured data onto the first two principal components is ca. 96%. The "x" symbol shown in FIG. 4 corresponds to the projection of the amplitude attenuation and phase retardation data for a randomly chosen bottle of the 1979 Petrus Pomerol measured on a different day.

Discussion

It is important to begin this section by mentioning the important result that at frequencies less than 25 MHz significant electrical signals are only observed on the lower electrode shown in FIG. 1 when a liquid is contained in the wine bottle. Removal of the liquid substantially attenuates the electrical signal while increasing the ionic strength of liquid increases the signal. Having established this fact, two extremely attractive features of the apparatus shown in FIG. 1 are simplicity and flexibility. Clearly the most direct approach to accomplish this experiment involves using a digital LCR meter, network analyzer, or vector impedance meter. (Kremer, F.; Schonhals, A., *Broadband Dielectric Spectroscopy*. Springer: Berlin, 2003.) These particular options are not attractive here as the increased ease of use with added features in the commercial-off-the-shelf device sacrifice necessary flexibility in the other aspects of the measurement such as broadcast and reception signal amplification and real time signal averaging and data processing. The only customized part(s) in the entire assembly are the circular copper electrode straps shown as black horizontal lines 105 and 110 on the wine bottle in FIG. 1 and the transimpedance amplifier (Horowitz, P.; Hill, W., *The Art of Electronics*. 2nd ed.; Cambridge University Press: Cambridge, 1989). The use of circular electrodes allows the effects of bottle thickness and glass content variations around the bottle circumference on the measured signal to be minimized as long as the electrode separation is maintained. As a comparison, the use of more standard parallel plate electrodes yields signals that are more strongly bottle dependent instead of bottle contents dependent. Coupling of the electric field into the wine bottle with circular electrode straps is superb, despite having been manually wrapped around the bottle for each measurement.

The overly simplified description of dielectric absorption provided in Section 2 was included to underscore the fact that the amplitude attenuation and phase retardation of the measured electric field with respect to the amplitude and phase of the applied electric field is related to the specific contents of the wine bottle captured in the frequency dependence of the $\chi(\omega)'$ and $\chi(\omega)''$ electric susceptibilities. It should be clear that the steady state theory is really only appropriate for the most ideal conditions where very slow frequency sweeps or point-by-point frequency changes are applied and where electrode geometry, sample container, and electric field coupling effects are neglected. (Kaatze, U.; Feldman, Y., Broadband Dielectric Spectrometry of Liquids and Biosystems. *Measurement Science and Technology* 2006, 17, R17-R35.) Since rapid frequency sweeps are applied in this study to various wine bottle shapes, actual estimates of $\chi(\omega)'$ and $\chi(\omega)''$ were not obtained here. Rather it is the bottle-to-bottle or wine-to-wine or vintage-to-vintage variation of the measured electrical response that is the basis for this wine authentication approach. In other words, it is the empirical variation of the measured signal for a suspect counterfeit bottle as a function of wine bottle contents in comparison to the signal for a known authentic bottle that is central to this method. This is in contrast to a microscopic approach where measured signals are reduced to solute identity and concentration values via a theory that accounts for the relationship of the electric field coupling to the $\chi(\omega)'$ and $\chi(\omega)''$ electric susceptibilities. Even with all of these qualifiers, the measured electrical responses obtained with the apparatus shown in FIG. 1 are proportional to the $\chi(\omega)'$ and $\chi(\omega)''$ electric susceptibilities.

Practically accessible electric field frequency sweep rates appear to have little effect on the measured data. A decrease in the total frequency sweep time from 10 s to 1 s in the low frequency band and from 10 s to 100 ms in the high frequency band does not change the frequency dependence of either the measured amplitude attenuation or phase retardation suggesting that subtle changes in wine constituents captured as small changes to $\chi(\omega)'$ and $\chi(\omega)''$ can propagate into wine dependent electrical responses provided that an appropriate applied electric field frequency range is used.

All electrical absorption data was obtained in two frequency blocks where the separation between the two regions was dictated by the lowest operation frequency of the MINI-CIRCUITS ZSC-2-I frequency splitter. The performance of the splitter at $\upsilon > 150$ kHz frequencies was superb while at $\upsilon < 150$ kHz serious amplitude attenuation, waveform distortion, and unequal output amplitudes were noticed. These deleterious effects could be avoided at low $\upsilon < 25$ kHz frequencies by operation with a BNC tee.

An electric field can interact with the charge, dipole moment, or susceptibility of small molecules and ions in liquid phase. The functional form of $\chi(\omega)'$ and $\chi(\omega)''$ depends on the charge, size, and molecular electron distribution for each ion or molecule in addition to the concentration of that ion or molecule in the liquid. This relationship between liquid composition and $\chi(\omega)'$ and $\chi(\omega)''$ suggests that there may be certain applied electric field frequencies that probe different aspects of wine. To address how the sensitivity of the dielectric absorption depends on major wine constituents, the five separate three sample libraries shown in Table 1 were prepared. Each sample library had an added deionized water sample thus increasing the membership to four solutions. The amplitude attenuation and phase retardation in both the low and high frequency blocks were obtained for each sample in the five library set shown in Table 1.

Principal component analysis was performed for each of the five libraries of four samples each and the first principal component based on amplitude attenuation (a) and phase retardation (b) for each library is shown for the low and high frequency blocks in FIGS. 2 and 3 respectively. As mentioned in the Results section, the dielectric absorption spectra for the sucrose sample were independent of concentration and the corresponding $P_1$ for that library is not included in FIGS. 2 and 3. The lack of sensitivity of the method towards sucrose is to be expected as the primary interaction mechanism between the electric field and the sucrose molecule is susceptibility, an effect that dramatically improves as the applied electric field frequency increases by three orders of magnitude into the GHz range. Since ca. 94% of the library variance is captured by $P_1$, the plots shown in FIGS. 2 and 3 report the maximum library variance at a particular frequency. It is important to note that these abscissa values correspond to frequencies that are the conjugate variable of time provided by the Fourier analysis of the measured waveforms. These frequencies may or may not directly correspond to the instantaneous frequency of the applied frequency swept electric field. In the limit that the dielectric relaxation rate is much larger than the frequency sweep rate the conjugate Fourier variable is the instantaneous applied frequency, otherwise it is not.

Figure 2A:
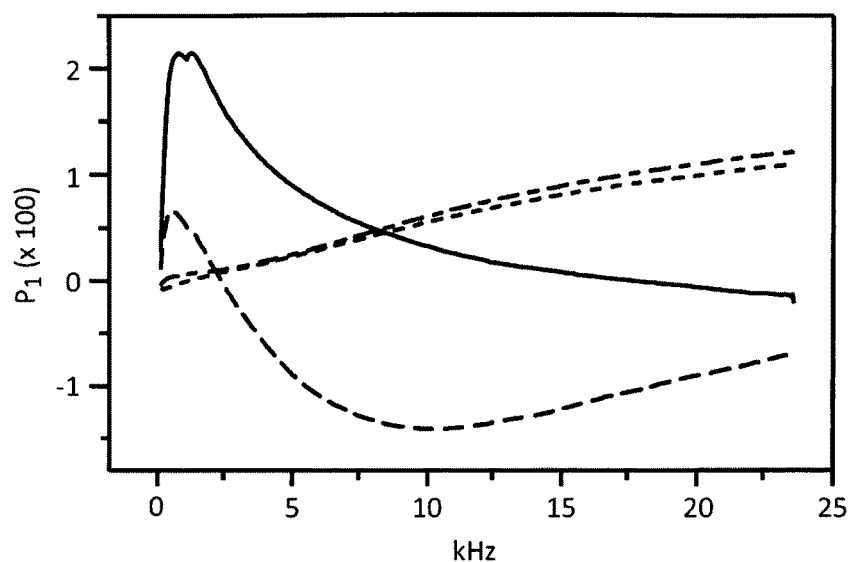
FIG. 2 provides a plot of the first principal component P1 in the 0<v<24 kHz frequency range based on the amplitude (a) and phase retardation (b) for the glycerol (solid line), ethyl alcohol (long dashed line), potassium sulfate (short dashed line), and acetic acid (long/short dashed line) libraries. The response for the sucrose samples was flat across this frequency band and was therefore not included in the plot.
Figure 2B:
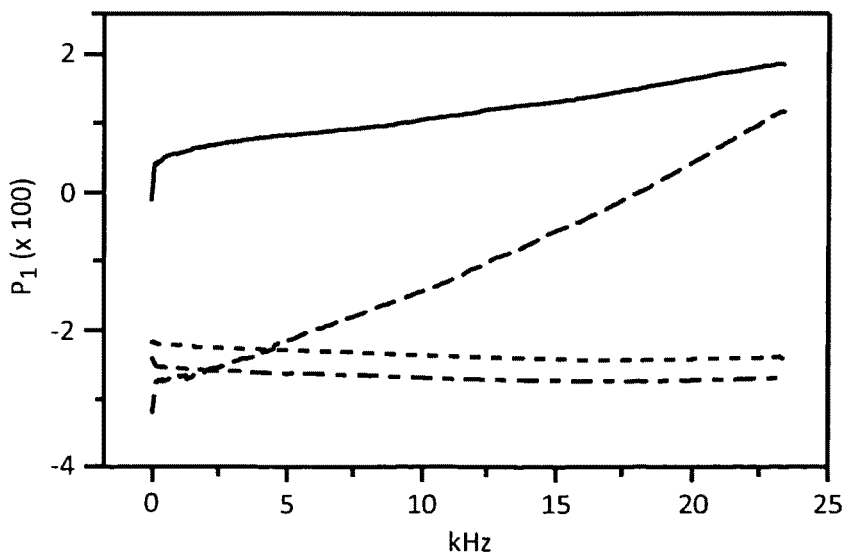
Figure 3A:
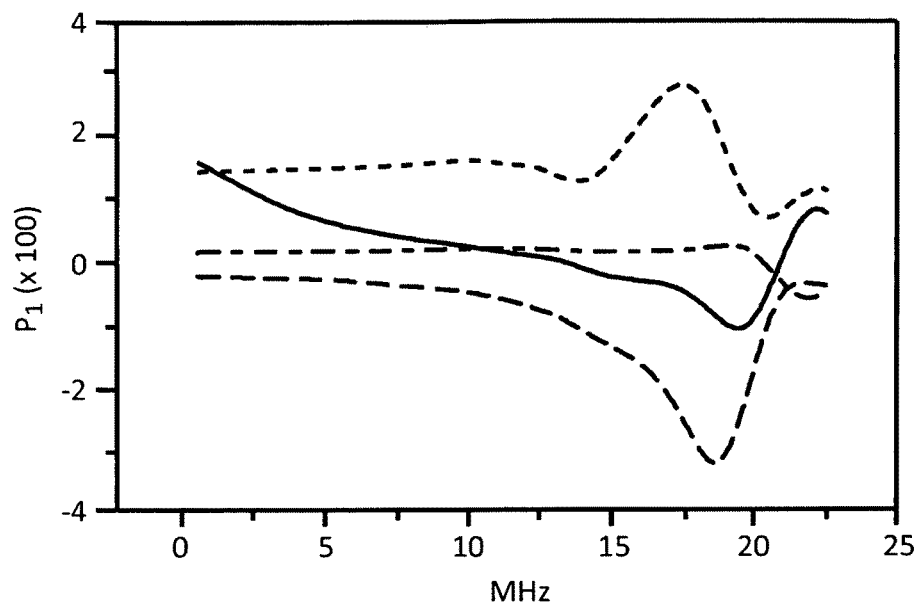
FIG. 3 provides plots of the first principal component P1 in the 150 kHz<v≤24 MHz frequency range based on the amplitude (a) and phase retardation (b) for the glycerol (solid line), ethyl alcohol (long dashed line), potassium sulfate (short dashed line), and acetic acid (long/short dashed line) libraries. The response for the sucrose samples was flat across this frequency band and was therefore not included in the plot.
Figure 3B:
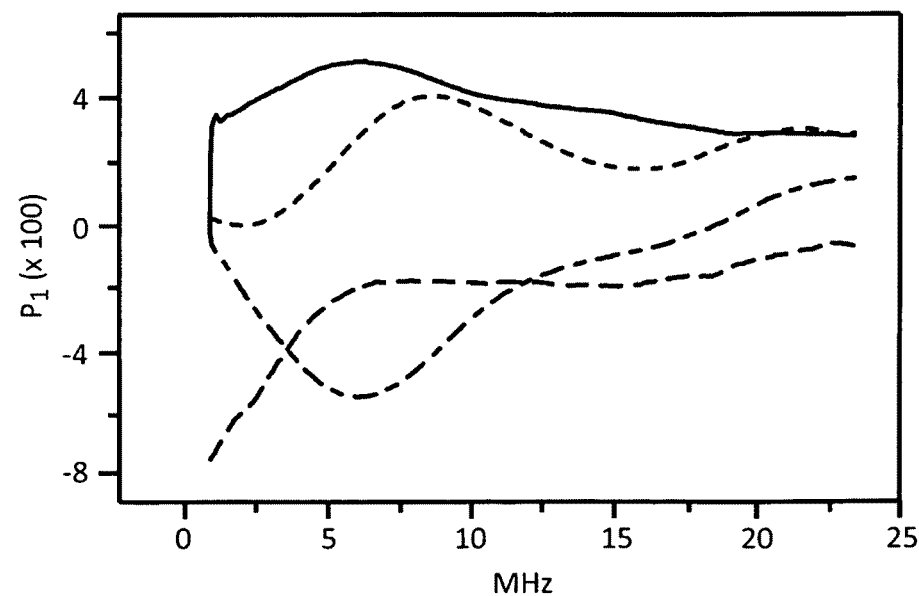

Analysis of FIGS. 2 and 3 shows that the $P_1$ shapes for the largely molecular solutes glycerol (solid line) and ethyl alcohol (long dashed line) are similar and different than those for the ionic solutes potassium sulfate (short dashed line) and acetic acid (long/short dashed line), especially in the lower frequency case shown in FIG. 2. The overall $P_1$ shape similarity for the largely molecular solutes is also observed in the higher frequency region in FIG. 3. It should be clear from the plots shown in FIGS. 2 and 3 that the different frequencies contain varying degrees of dynamic information. For example, in the case of the small molecule solutes, there is a substantial solute concentration data variance below 2.5 kHz revealed in the amplitude attenuation data at low frequency as shown in FIG. 2(a). A similar observation is made above 20 kHz for the largely molecular solutes in the phase retardation based $P_1$ plot shown in FIG. 2(b). The higher frequency $P_1$ plots shown in FIG. 3 have two distinct variance rich regions where all solutes, molecular or ionic, yield dramatically different results. The 15 MHz<$\nu$<20 MHz range in FIG. 3(a) and the 3 MHz<$\nu$<10 MHz range in FIG. 3(b) identifies these particular frequencies. The simple fact that the different solutes at the concentrations anticipated for wine yield distinctly different, resolvable, and detectable $P_1$ eigenvectors suggests that dielectric absorption spectroscopy, in particular the apparatus shown in FIG. 1, can be used to authenticate wine as the transformed data provides measurable changes as a function of the solute concentration.

The $P_1$ plots shown in FIGS. 2 and 3 illustrate that different solutions lead to different specific electric responses and that different frequencies are more sensitive to solute identity than others. The plots however reveal nothing about the overall sensitivity of the dielectric absorption approach to a given solute, other than the lack of a concentration dependent response for the sucrose solutions, an observation that implies that the method is insensitive to natural sugar concentrations in wine. Principal component analysis can be used to estimate this solute sensitivity by determining the slope $dx^q/d[\text{solute}]$ of a data record projected onto the first principal component of the library $x_q$ as a function of concentration. The results of this sensitivity estimate are provided in the right hand column in Table 1. It should not be surprising that in the $\nu < 25$ MHz frequency region the dielectric absorption is most sensitive to ionic solutes (potassium sulfate) and correspondingly less sensitive to molecular solutes (glycerol) as the major contribution to the bulk dielectric response at low frequencies is the migration of free charge since the dipole orientation and molecular polarization of small molecules is minimal at low frequency as dictated by the rotational relaxation times of these processes in liquids (Behrends, R.; Fuchs, K.; Kaatze, U.; Hayashi, Y.; Feldman, Y., Dielectric Properties of Glycerol/Water Mixtures at Temperatures Between 10 and 50 C. *The Journal of Chemical Physics* 2006, 124, 1445112; Peton, P.; Pottel, R.; Kaatze, U., Water-Ethanol Mixtures at Different Compositions and Temperatures. A Dielectric Relaxation Study. *Journal of Physical Chemistry* 2000, 104, 7420-7428.) The source of charge migration in liquids can be extrinsic or intrinsic in nature as in the case of free ion translation and proton transfer among hydrogen bonds respectively. If the sole contribution to the measured dielectric response were due to extrinsic properties, the concentration of free charge should dictate sensitivity. Hence, a completely dissociated compound would show a greater sensitivity than a partially dissociated compound of equal concentration. The total ionic strengths corresponding to the largest solution concentrations shown in Table 1 are $4.1\times 10^{-2}$ M, $2.2\times 10^{-2}$ M, $1.193\times 10^{-7}$ M, and $1.02\times 10^{-7}$ M for potassium sulfate, acetic acid, glycerol and ethyl alcohol respectively. This analysis suggests that in the potassium sulfate and acetic acid solutions the extrinsic contribution dominates, an argument that does not explain the absolute sensitivity observed for glycerol or ethyl alcohol as Table 1 indicates that the measured sensitivity drops by just an order of magnitude for these compounds, not the roughly five orders of magnitude anticipated on the basis of ionic strength alone. This larger than expected observed sensitivity for glycerol and ethyl alcohol is likely due to a dynamic glass transition resulting from the strong hydrogen bonding of these compounds (Puzenko, A.; Hayashi, Y.; Ryabov, Y.; Balin, I.; Feldman, Y.; Kaatze, U.; Behrends, R., Relaxation Dynamics in Glycerol-Water Mixtures: I. Glycerol-Rich Mixtures. *Journal of Physical Chemistry* 2005, 109, 6031-6035) Indeed the dielectric loss of glycerol/water solutions has a maximum at approximately 10 MHz (Behrends, R.; Fuchs, K.; Kaatze, U.; Hayashi, Y.; Feldman, Y., Dielectric Properties of Glycerol/Water Mixtures at Temperatures Between 10 and 50° C. *The Journal of Chemical Physics* 2006, 124, 1445112) that has been attributed to this transition. Although the dielectric loss for ethyl alcohol/water solutions is smaller than the corresponding loss for an equimolar amounts of glycerol/water solutions because the glass structure is more difficult to form with a single hydroxide in comparison to a triple hydroxide, the simple fact that there is six times more ethyl alcohol than glycerol in wine and the test solutions could explain the sensitivity ordering for these two compounds in Table 1. Equally possible is the fact that both glycerol and ethyl alcohol modify the viscosity of pure water and it may be that it is this effect that explains the sensitivity ordering for these solutes in Table 1. It is likely however that all three mechanism, ionic strength, glass transition loss, and viscosity effects operate together and lead to the sensitivity ordering of glycerol and ethyl alcohol.

Figure 4:
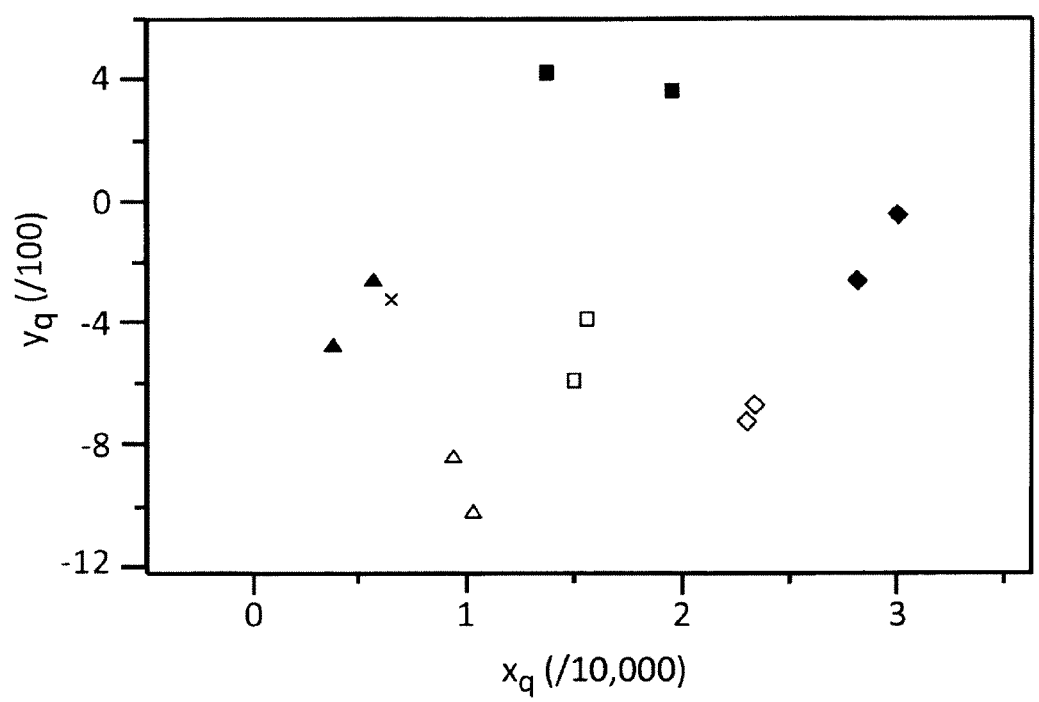
FIG. 4 provides projections of the measured amplitude attenuation and phase retardation data for a twelve bottle collectible wine library onto the first $P_1$ and second $P_2$ principal components to obtain the respective $x_q$ and $y_q$ coordinates. The closed and open squares correspond to the 1985 and the 2002 vintages of OPUS ONE respectively, the closed and open lozenges correspond to the 1958 and 1990 vintages of GRAND VIN DE CHATEAU LATOUR respectively, and the closed and open triangles correspond to the 1979 and 1994 vintages of Petrus Pomerol respectively. The "x" symbol corresponds to the projection of the amplitude and phase retardation data onto $P_1$ and $P_2$ for a randomly chosen bottle of the 1979 Petrus Pomerol measured on a different day.

It should be clear from FIGS. 2 and 3 and from the sensitivity estimates shown in Table 1 that this full bottle low frequency dielectric absorption method is sensitive to the natural solute concentrations in wine. To test whether or not the approach is applicable to wine, a twelve bottle rare wine library was obtained and screened with the apparatus shown in FIG. 1. Application of PCA to both the amplitude attenuation and phase retardation data for each bottle yields the first two principal components $P_1$ and $P_2$, vectors that can be used with the measured data $d_q$ to calculate $x_q$ and $y_q$ values for each wine from Eqs. (13) and (14) respectively. FIG. 4 shows the $x_q$ and $y_q$ values for each of the full intact bottled wines as solid and open symbols. The like symbols obviously group in this two dimensional representation and it is this grouping that can be used to identify counterfeit wines in comparison to authentic library standards. As an example of how this protocol would operate, consider the solid and open symbols in FIG. 4 as a reference library. A bottle of the 1979 Petrus Pomerol was randomly chosen from the library, re-scanned using the apparatus shown in FIG. 1, and treated with PCA to yield the "x" shown in FIG. 4. The proximity of the "x" symbol to the solid triangles established by earlier measurements for the 1979 Petrus Pomerol suggests that the re-scanned bottle is in fact the 1979 Petrus Pomerol. The degree of uncertainty in this claim can be obtained from bivariate statistics when needed. Such an estimate was not accomplished here as more than two library data points are required to accomplish such a treatment.

It is important to mention that this wine authentication protocol requires access to known authentic bottles of wine. This fact is not a limitation as the same requirement holds for the analysis of open bottles, either by human sensory or instrumental means. A professional sommelier will only be able to comment on the authenticity of a particular wine if he or she has sampled that wine. An instrumental approach will yield specific solute concentrations in a suspect wine and an authenticity judgment is only possible if the actual concentrations for a known authentic bottle were available. There is one important exception to this last statement, based on the fact that radionuclide levels in ground water increased at the dawn of the nuclear age. Therefore wines bottled before 1945 will have noticeably different radionuclide levels than those bottle after 1945. This fact has been used to show that the famous Thomas Jefferson wine bottles were in fact counterfeits. Frank, M. "Jefferson Bottle" Collector Strikes Back. Wine spectator website on the world wide web at winespectator.com/Wine/Features/0,1197,4252,00.

All measurements reported here were accomplished at room temperature, and results not shown here reveal that the method has a strong temperature dependence. This issue was avoided in the measurements reported here by always operating at the constant 20° C. room temperature. This means that if a library is collected at room temperature, the analysis of a suspect counterfeit bottle must also be performed at room temperature. However, if the library was prepared at different temperatures, then the temperature dependence of the library data could be determined and the analysis of a suspect counterfeit bottle could be performed at any reasonable temperature, even in a humid, cool wine cellar environment.

Example 2

Methods of Authentication of Full Intact Wine Bottles Using Magnetic Susceptibility Based Fingerprinting Experimental All chemicals were obtained from Sigma-Aldrich and used without further purification. Sixteen bottles of CHARLES SHAW wine obtained from TRADER JOE'S were drained, cleaned, and refilled with solutions of de-ionized water and ethyl alcohol, acetic acid, potassium sulfate, glycerol, and sucrose. One bottle filled with de-ionized water served as a standard solution while the remaining fifteen were filled with five sets of three solutions of each of these compounds as described in Table 2. The solution concentrations were chosen to bracket the mean amounts reported for wine. Six sets of two duplicate bottles of collectible wine including the 1990 GRAND VIN DE CHATEAU LATOUR, the 1958 GRAND VIN DE CHATEAU LATOUR, the 2002 OPUS ONE, the 1985 OPUS ONE, the 1994 Petrus Pomerol, and the 1979 Petrus Pomerol were used to construct a wine authentication library. The spectrometer shown in FIG. 6 was used to measure the room temperature magnetic properties of the prepared full bottle solutions and the collectible wine in the 500 Hz$<\upsilon<$30 MHz frequency range in steps of 2 MHz. Here the output of a Stanford Research Systems SRS DS345 function generator was sent into an ENI 403LA 3 Watt r.f. amplifier whose output $I_p$ was then used to drive the primary coil. The voltages induced in top half $V_s$ and bottom half $V_r$ of the gradiometer coil were then sent into MINI-CIRCUITS ZAD-1 mixers whose LO port is driven by the output of a MINI-CIRCUITS ZSC-2-1 split second phase locked SRS DS345 operating 1 kHz lower in frequency. The IF outputs of the mixers were directed into a Krohn-Hite 3940 operating as a low pass filter with 20 dB of gain on each channel. This filtering/gain step effectively removes the difference frequency and enhances signal strength. The output channel of the Krohn-Hite 3940 corresponding to the sample voltage $V_s$ is directed into one port of an INA 103KP instrumentation amplifier while the other output channel of the Krohn-Hite 3940 corresponding to the reference voltage $V_r$ is directed into an Analog Devices OP27EZP configured as an all-pass amplifier and then another Analog Devices OP27EZP configured as an inverting gain amplifier prior to being inserted into the other INA 103KP instrumentation amplifier port. This configuration of the detection electronics allows the dynamic range of the measurement to be dramatically improved by adjusting the OP27EaZP R1, R2, R3, and R4 resistors to null the $V_s$-$V_r$ signal for a standard sample of deionized water at each frequency prior to the measurement of real wines at that frequency. Operation in this way effectively background subtracts the effects of both container and solvent on the measured signal leaving only contributions from the remainder of wine solutes. The amplitude and phase of the difference signal from the output of the instrumentation amplifier corresponding to the $V_s$-$V_r$ signal is then measured with a Stanford Research Systems SRS530 lock-in amplifier. A third phase locked Stanford Research Systems SRS345 was used as a reference for the lock-in amplifier. All measurements were accomplished at room temperature, 20° C.

All data processing was accomplished using Matlab. Amplitude and phase values were obtained for each bottle starting at 500 Hz extending to 30 MHz in steps of 2 MHz. These values were then compiled into a master data matrix whereupon PCA was applied as a means of dimensional reduction. The resultant first two principle components contained 97% of the variance and thus the remaining dimensions were discarded.

Results

The diamagnetic response for each of the samples shown in Table 2 was obtained in the 500 Hz<υ<30 MHz frequency range using the apparatus shown in FIGS. 5 and 6 as described in the Experimental section. The amplitude attenuation and phase retardation of the input stepped frequency input due to diamagnetic absorption for the three separate solution concentrations for each solute along with the same data for the pure solvent de-ionized water was used to construct a sample library. In this way four separate four sample libraries were created to demonstrate the solution dependence of the dielectric absorption of specific wine constituents. The right hand column in Table 2 corresponds to the sensitivity of the method to expected natural solute concentrations, a number that is determined from the slope of the projection of the measured amplitude attenuation and phase retardation values for a given solute concentration onto the first principal component for the entire solute concentration library. The diamagnetic responses for the twelve collectible wines was obtained in the 500 Hz<υ<30 MHz frequency range in 2 MHz steps as described in the Experimental section. The amplitude attenuation and phase retardation at each frequency for each bottle was used to construct a library.

TABLE 2

| Solute | Concentration | | | Sensitivity |
| --- | --- | --- | --- | --- |
| | Sample 1 | Sample 2 | Sample 3 | |
| ethyl alcohol | 20.00 ± 0.01% (v/v) | 13.00 ± 0.01% (v/v) | 5.00 ± 0.01% (v/v) | 0.93 ± 0.02 |
| acetic acid | 3.75 ± 0.05 mL/L | 2.25 ± 0.05 mL/L | 0.375 ± 0.05 mL/L | 20.74 ± 0.15 |
| potassium sulfate | 2.39 ± 0.01 g/L | 0.747 ± 0.01 g/L | 0.253 ± 0.01 g/L | 65.51 ± 0.08 |
| glycerol | 19.78 ± 0.01 g/L | 10.00 ± 0.01 g/L | 4.02 ± 0.01 g/L | 0.75 ± 0.01 |

Figure 7:
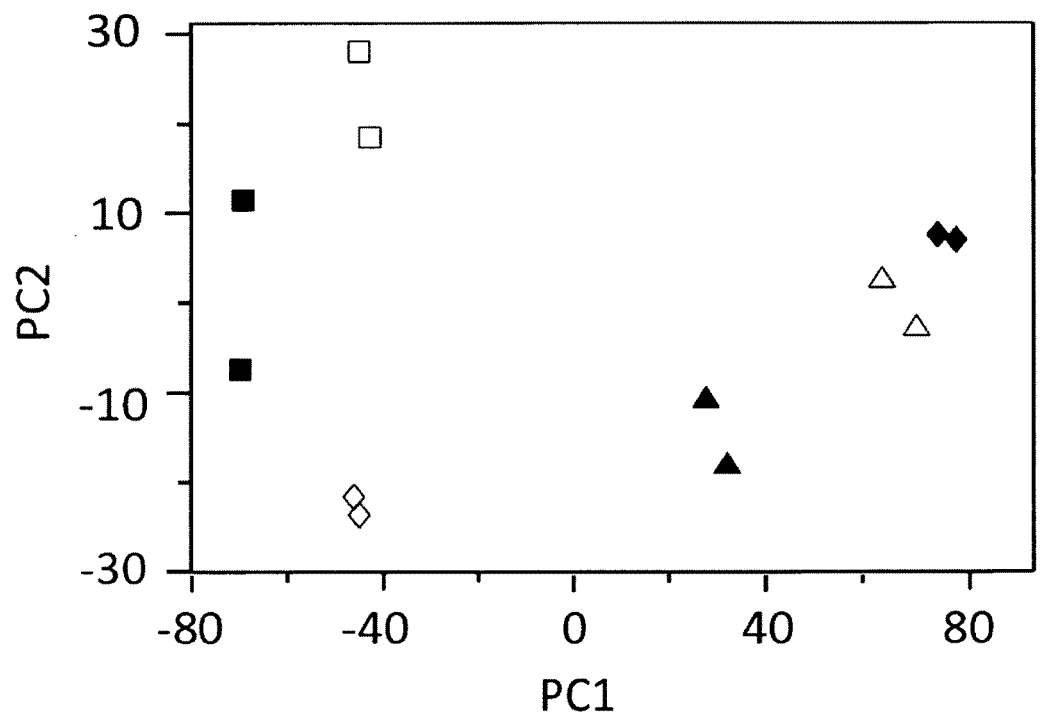
FIG. 7 provides data for magnetic susceptibility of the contents of a wine bottle analyzed in a system of FIG. 6. Principle components Pt and $P_2$ are shown for 1985 and 2002 vintages of OPUS ONE (open and closed squares respectively) and for 1958 and 1990 vintages of GRAND VIN DE CHATEAU LATOUR (open and closed lozenges or diamonds respectively) and for 1979 and 1994 vintages of Petrus Pomerol (open and closed triangles respectively).

Principal component analysis followed by projection of the amplitude attenuation and phase retardation data for a given bottle onto the first two principal components PC1 and PC2 coordinate values for each bottle shown in the plot in FIG. 7. Here the closed and open squares correspond to the 1985 and the 2002 vintages of OPUS ONE respectively, the closed and open lozenges correspond to the 1958 and 1990 vintages of GRAND VIN DE CHATEAU LATOUR respectively, and the closed and open triangles correspond to the 1979 and 1994 vintages of Petrus Pomerol respectively. In this case, the percentage of the total variance captured by projecting the measured data onto the first two principal components is 97%.

Conclusion

The design and construction of a non-invasive, non-destructive full intact wine bottle screening device is provided. The method uses wine type and vintage dependent changes in the low frequency (ν<25 MHz) dielectric absorption of wine or low frequency (ν<30 MHz) diamagnetic absorption of wine combined with PCA to authenticate wine by comparing the results for suspicious bottles to library data, e.g., a known bottle. The basic idea and the sensitivity of the approach have been tested by screening prepared solution libraries and by analyzing the results with PCA. These tests suggest that the approach is most sensitive to ionic salts in solution, acids and bases, and small molecules and noticeably less sensitive to larger molecular solutes like sucrose. Although operation at higher microwave frequencies would enhance the response for sugars, the correspondingly shorter wavelength involved would introduce unwanted electrical reflections in the wine bottle, an additional unwanted experimental problem that would have to be solved. Application of the new approach to a twelve bottle rare wine library indicates that like wines group in a two dimensional plot of the projections of the measured data on the first two principal components of the library. It is clear from these results that it is possible to use low frequency dielectric absorption or diamagnetic absorption to authenticate wine with the help of PCA. As long as acceptable rare wine standards are available and the acquisition temperature of the library is the same as that for the suspect bottle, this study indicates that authentication and thus the defeat of current wine counterfeiting efforts are possible using portable commercial-off-the-shelf instrumentation as provided herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, a sealed container, of any shape, comprising beverages or liquids other than wine can be used with the apparatus of the invention. In addition, the annular electrodes that ring the container can be any shape so long as they completely encircle and contact the container. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. An apparatus for analyzing a sealed container comprising:
   a) a waveform generator, which waveform generator is capable of producing a frequency swept electrical field;
   b) a first solenoid coil operably coupled to the waveform generator, which solenoid produces a magnetic field;
   c) a gradiometer comprising a top sample solenoid coil and a lower reference solenoid coil, wherein the top sample solenoid coil and the lower reference solenoid coil are counter-wound with respect to each other, wherein the gradiometer is positioned within the first coil, and wherein the container can be positioned within the top sample solenoid coil;
   d) a receiver operably coupled to the top sample solenoid coil, which receiver is capable of capturing a set of empirical data points reflecting a change in the magnetic field due to the contents of the container; and
   e) a computer operably coupled to the receiver and configured to empirically compare data from the set of empirical data points to known magnetic field empirical data from a known contents sealed container and thereby identify or authenticate the contents of the sealed container.

2. The apparatus of claim 1, wherein the top sample solenoid coil is coupled to the receiver via an instrumentation amplifier.

3. The apparatus of claim 2, wherein the instrumentation amplifier is operably coupled to an inverting gain amplifier, the inverting gain amplifier is operably coupled to an all-pass amplifier, and the all-pass amplifier is operably coupled to the lower reference solenoid coil.

4. The apparatus of claim 1, wherein the sealed container is an intact bottle of wine.

5. The apparatus of claim 1, further wherein the computer is configured for data analysis.

6. The apparatus of claim 5, wherein the data analysis is a statistical method.

7. The apparatus of claim 6, wherein the statistical method is principal component analysis.

8. The apparatus of claim 1, further comprising the sealed container, which sealed container comprises a wine bottle positioned within the top sample solenoid coil.

9. A method of authenticating a test bottle of wine, the method comprising:
   a) measuring a change in a magnetic field when applied to a standard bottle of wine positioned within a gradiometer comprising a top sample solenoid coil and a lower reference solenoid coil thereby producing a first set of empirical data,
   wherein the standard bottle of wine is positioned within the top sample solenoid coil,
   wherein the top sample solenoid coil and the lower reference solenoid coil are counter-wound with respect to each other,
   wherein the gradiometer is positioned within a first solenoid coil operably coupled to a waveform generator capable of producing a frequency swept electrical field,
   wherein the magnetic field is applied using the frequency swept electric field applied to the first solenoid coil, and
   wherein the frequency of the electric field ranges from about 500 Hz to about 30 MHz;
   b) applying a magnetic field to a test bottle of wine positioned within the gradiometer comprising the top sample solenoid coil and the lower reference solenoid coil, and measuring a change in the magnetic field, thereby producing a second set of empirical data,
   wherein the test bottle of wine is positioned within the top sample solenoid coil,
   wherein the magnetic field is applied using a frequency swept electric field applied to the first solenoid coil, and
   wherein the frequency of the electric field ranges from about 500 Hz to about 30 MHz;
   c) applying statistical analysis to the first and second set of empirical data to produce a first magnetic susceptibility profile and a second magnetic susceptibility profile; and
   d) comparing the first magnetic susceptibility profile from the standard bottle and the second magnetic susceptibility profile from the test bottle, thereby determining if the test bottle of wine is the same as the standard bottle of wine.

10. The method of claim 9, wherein producing the second set of empirical data comprises generating a sample voltage $V_s$ from the top sample solenoid coil, generating a reference voltage $V_r$ from the lower reference solenoid coil, and measuring the voltage difference $V_s - V_r$.

11. The method of claim 10, wherein measuring the voltage difference $V_s - V_r$ comprises:
   directing the sample voltage $V_s$ to an instrumentation amplifier and
   directing the reference voltage $V_r$ to an all-pass amplifier, wherein the all-pass amplifier is operably linked to an inverting gain amplifier, and wherein the inverting gain amplifier is operably linked to the instrumentation amplifier.

12. The method of claim 9, wherein the statistical analysis comprises principal component analysis.

13. The method of claim 9, wherein the test bottle of wine comprises an intact bottle of wine.

14. The method of claim 9, wherein the test bottle of wine is a full sealed bottle of wine.

15. The method of claim 9, wherein the change in the magnetic field comprises phase retardation or amplitude attenuation.

16. A method of authenticating a test sealed container, the method comprising:
   a) measuring a change in a magnetic field when applied to a known contents sealed container positioned within a gradiometer comprising a top sample solenoid coil and a lower reference solenoid coil thereby producing a first set of empirical data,
   wherein the known contents sealed container is positioned within the top sample solenoid coil, wherein the top sample solenoid coil and the lower reference solenoid coil are counter-wound with respect to each other,
wherein the gradiometer is positioned within a first solenoid coil operably coupled to a waveform generator capable of producing a frequency swept electrical field,
wherein the magnetic field is applied using the frequency swept electric field applied to the first solenoid coil, and
wherein the frequency of the electric field ranges from about 500 Hz to about 30 MHz;
b) applying a magnetic field to a test sealed container positioned within the gradiometer comprising the top sample solenoid coil and the lower reference solenoid coil, and measuring a change in the magnetic field, thereby producing a second set of empirical data,
wherein the test sealed container is positioned within the top sample solenoid coil,
wherein the magnetic field is applied using a frequency swept electric field applied to the first solenoid coil, and
wherein the frequency of the electric field ranges from about 500 Hz to about 30 MHz;
c) applying statistical analysis to the first and second set of empirical data to produce a first magnetic susceptibility profile and a second magnetic susceptibility profile; and
d) comparing the first magnetic susceptibility profile from the known contents sealed container and the second magnetic susceptibility profile from the test sealed container, thereby determining if the test sealed container is the same as the known contents sealed container.

\* \* \* \* \*